(12) United States Patent
Barrera et al.

(10) Patent No.: US 11,883,028 B2
(45) Date of Patent: Jan. 30, 2024

(54) SYSTEMS AND METHODS FOR POST-OPERATIVE ANASTOMOTIC LEAK DETECTION

(71) Applicant: Covidien LP, Mansfield, MA (US)

(72) Inventors: Osvaldo A. Barrera, Madison, CT (US); David N. Heard, Boulder, CO (US); Jeffrey A. Miller, East Haven, CT (US); Kasey A. Grim, Lafayette, CO (US); Joe Sartor, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 205 days.

(21) Appl. No.: 17/468,756

(22) Filed: Sep. 8, 2021

(65) Prior Publication Data
US 2023/0076424 A1    Mar. 9, 2023

(51) Int. Cl.
| | | |
|---|---|---|
| *A61B 17/064* | (2006.01) | |
| *A61B 17/115* | (2006.01) | |
| *A61B 17/11* | (2006.01) | |
| *A61B 17/00* | (2006.01) | |

(52) U.S. Cl.
CPC ....... *A61B 17/1155* (2013.01); *A61B 17/1114* (2013.01); *A61B 2017/00004* (2013.01); *A61B 2017/00084* (2013.01); *A61B 2017/00199* (2013.01)

(58) Field of Classification Search
CPC .................. A61B 17/1114; A61B 17/1155
See application file for complete search history.

(56) References Cited

U.S. PATENT DOCUMENTS

| | | |
|---|---|---|
| 3,193,165 A | 7/1965 | Akhalaya et al. |
| 3,388,847 A | 6/1968 | Kasulin et al. |
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |

(Continued)

FOREIGN PATENT DOCUMENTS

| | | |
|---|---|---|
| CA | 908529 A | 8/1972 |
| CA | 2805365 A1 | 8/2013 |

(Continued)

OTHER PUBLICATIONS

International Search Report and Written Opinion issued in corresponding International Application No. PCT/IB2022/058355 dated Dec. 15, 2022, 17 pages.

(Continued)

*Primary Examiner* — Eyamindae C Jallow
(74) *Attorney, Agent, or Firm* — Carter, DeLuca & Farrell LLP

(57) ABSTRACT

A tissue monitoring system includes a sensor, a sensor reader, and at least one computing device. The sensor is releasably coupled to a staple by a tether and is configured to measure a physiological parameter of tissue and convert the measurement into a signal. The sensor reader is configured to receive the signal from the sensor and the at least one computing device is configured to receive the signal from the sensor reader and process the signal into physiological data. The sensor is implanted in tissue by the staple.

20 Claims, 16 Drawing Sheets

(56) References Cited

U.S. PATENT DOCUMENTS

| | | |
|---|---|---|
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,930,674 A | 6/1990 | Barak |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,383,880 A | 1/1995 | Hooven |
| 5,389,098 A | 2/1995 | Tsuruta et al. |
| 5,392,979 A | 2/1995 | Green et al. |
| 5,395,030 A | 3/1995 | Kuramoto et al. |
| 5,395,033 A | 3/1995 | Byrne et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,144 A | 11/1995 | Guy et al. |
| 5,464,415 A | 11/1995 | Chen |
| 5,470,006 A | 11/1995 | Rodak |
| 5,474,223 A | 12/1995 | Viola et al. |
| 5,476,206 A | 12/1995 | Green et al. |
| 5,497,934 A | 3/1996 | Brady et al. |
| 5,503,635 A | 4/1996 | Sauer et al. |
| 5,518,163 A | 5/1996 | Hooven |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,782,397 A | 7/1998 | Koukline |
| 5,799,857 A | 9/1998 | Robertson et al. |
| 5,814,055 A | 9/1998 | Knodel et al. |
| 5,833,603 A | 11/1998 | Kovacs et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,902,236 A | 5/1999 | Iversen |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |

(56) References Cited

U.S. PATENT DOCUMENTS

| | | |
|---|---|---|
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,486,588 B2 | 11/2002 | Doron et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,125,382 B2 | 10/2006 | Zhou et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,297,112 B2 | 11/2007 | Zhou et al. |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,416,530 B2 | 8/2008 | Turner et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,657,297 B2 | 2/2010 | Simpson et al. |
| 7,669,747 B2 | 3/2010 | Weisenburgh, II et al. |
| 7,686,201 B2 | 3/2010 | Csiky |
| 7,686,762 B1 | 3/2010 | Najafi et al. |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |

(56) References Cited

U.S. PATENT DOCUMENTS

| | | |
|---|---|---|
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,356,740 B1 | 1/2013 | Knodel |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,479,968 B2 | 7/2013 | Hodgkinson et al. |
| 8,485,414 B2 | 7/2013 | Criscuolo et al. |
| 8,486,070 B2 | 7/2013 | Morgan et al. |
| 8,490,853 B2 | 7/2013 | Criscuolo et al. |
| 8,511,533 B2 | 8/2013 | Viola et al. |
| 8,529,599 B2 | 9/2013 | Holsten |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,627,995 B2 | 1/2014 | Smith et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,646,674 B2 | 2/2014 | Schulte et al. |
| 8,662,370 B2 | 3/2014 | Takei |
| 8,663,258 B2 | 3/2014 | Bettuchi et al. |
| 8,672,207 B2 | 3/2014 | Shelton, IV et al. |
| 8,672,931 B2 | 3/2014 | Goldboss et al. |
| 8,672,951 B2 | 3/2014 | Smith et al. |
| 8,678,264 B2 | 3/2014 | Racenet et al. |
| 8,679,137 B2 | 3/2014 | Bauman et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,695,864 B1 | 4/2014 | Hausen |
| 8,708,212 B2 | 4/2014 | Williams |
| 8,727,197 B2 | 5/2014 | Hess et al. |
| 8,733,611 B2 | 5/2014 | Milliman |
| 8,733,615 B2 | 5/2014 | Nalagatla et al. |
| 8,746,531 B2 | 6/2014 | Wenchell et al. |
| 8,746,532 B2 | 6/2014 | Nalagatla et al. |
| 8,783,543 B2 | 7/2014 | Shelton, IV et al. |
| 8,789,737 B2 | 7/2014 | Hodgkinson et al. |
| 8,800,838 B2 | 8/2014 | Shelton, IV |
| 8,800,841 B2 | 8/2014 | Ellerhorst et al. |
| 8,801,734 B2 | 8/2014 | Shelton, IV et al. |
| 8,801,735 B2 | 8/2014 | Shelton, IV et al. |
| 8,821,523 B2 | 9/2014 | Heinrich et al. |
| 8,827,903 B2 | 9/2014 | Shelton, IV et al. |
| 8,833,629 B2 | 9/2014 | Nalagatla et al. |
| 8,840,004 B2 | 9/2014 | Holsten et al. |
| 8,844,792 B2 | 9/2014 | Viola |
| 8,845,661 B2 | 9/2014 | D'Arcangelo et al. |
| 8,870,911 B2 | 10/2014 | Williams et al. |
| 8,875,974 B2 | 11/2014 | Rebuffat et al. |
| 8,893,948 B2 | 11/2014 | Williams |
| 8,910,847 B2 | 12/2014 | Nalagatla et al. |
| 8,915,866 B2 | 12/2014 | Nycz |
| 8,925,785 B2 | 1/2015 | Holsten et al. |
| 8,925,786 B2 | 1/2015 | Holsten et al. |
| 8,967,448 B2 | 3/2015 | Carter et al. |
| 8,978,955 B2 | 3/2015 | Aronhalt et al. |
| 9,010,608 B2 | 4/2015 | Casasanta, Jr. et al. |
| 9,010,612 B2 | 4/2015 | Stevenson et al. |
| 9,016,540 B2 | 4/2015 | Whitman et al. |

(56) References Cited

U.S. PATENT DOCUMENTS

| | | |
|---|---|---|
| 9,033,204 B2 | 5/2015 | Shelton, IV et al. |
| 9,095,340 B2 | 8/2015 | Felder et al. |
| 9,113,871 B2 | 8/2015 | Milliman et al. |
| 9,113,877 B1 | 8/2015 | Whitman et al. |
| 9,113,883 B2 | 8/2015 | Aronhalt et al. |
| 9,113,884 B2 | 8/2015 | Shelton, IV et al. |
| 9,113,885 B2 | 8/2015 | Hodgkinson et al. |
| 9,125,654 B2 | 9/2015 | Aronhalt et al. |
| 9,155,536 B1 | 10/2015 | Hausen et al. |
| 9,161,757 B2 | 10/2015 | Bettuchi |
| 9,204,881 B2 | 12/2015 | Penna |
| 9,211,122 B2 | 12/2015 | Hagerty et al. |
| 9,220,504 B2 | 12/2015 | Viola et al. |
| 9,232,941 B2 | 1/2016 | Mandakolathur Vasudevan et al. |
| 9,232,945 B2 | 1/2016 | Zingman |
| 9,289,207 B2 | 3/2016 | Shelton, IV |
| 9,301,763 B2 | 4/2016 | Qiao et al. |
| 9,307,994 B2 | 4/2016 | Gresham et al. |
| 9,326,773 B2 | 5/2016 | Casasanta, Jr. et al. |
| 9,351,729 B2 | 5/2016 | Orban, III et al. |
| 9,351,731 B2 | 5/2016 | Carter et al. |
| 9,364,229 B2 | 6/2016 | D'Agostino et al. |
| 9,370,366 B2 | 6/2016 | Mozdzierz |
| 9,370,367 B2 | 6/2016 | Mozdzierz |
| 9,393,014 B2 | 7/2016 | Milliman |
| 9,408,603 B2 | 8/2016 | Patel |
| 9,421,013 B2 | 8/2016 | Patel et al. |
| 9,445,817 B2 | 9/2016 | Bettuchi |
| 9,451,962 B2 | 9/2016 | Olson |
| 9,456,821 B2 | 10/2016 | Bettuchi et al. |
| 9,463,022 B2 | 10/2016 | Swayze et al. |
| 9,492,166 B2 | 11/2016 | Kostrzewski |
| 9,498,222 B2 | 11/2016 | Scheib et al. |
| 9,504,470 B2 | 11/2016 | Milliman |
| 9,522,005 B2 | 12/2016 | Williams et al. |
| 9,549,738 B2 | 1/2017 | Mandakolathur Vasudevan et al. |
| 9,572,572 B2 | 2/2017 | Williams |
| 9,579,102 B2 | 2/2017 | Holsten et al. |
| 9,592,055 B2 | 3/2017 | Milliman et al. |
| 9,592,056 B2 | 3/2017 | Mozdzierz et al. |
| 9,597,081 B2 | 3/2017 | Swayze et al. |
| 9,597,082 B2 | 3/2017 | Stokes et al. |
| 9,603,599 B2 | 3/2017 | Miller et al. |
| 9,629,624 B2 | 4/2017 | Hessler et al. |
| 9,636,112 B2 | 5/2017 | Penna et al. |
| 9,649,110 B2 | 5/2017 | Parihar et al. |
| 9,649,113 B2 * | 5/2017 | Ma .................... A61B 17/1155 |
| 9,668,740 B2 | 6/2017 | Williams |
| 9,675,348 B2 | 6/2017 | Smith et al. |
| 9,681,872 B2 | 6/2017 | Jankowski et al. |
| 9,681,873 B2 | 6/2017 | Smith et al. |
| 9,687,234 B2 | 6/2017 | Smith et al. |
| 9,693,773 B2 | 7/2017 | Williams |
| 9,700,309 B2 | 7/2017 | Jaworek |
| 9,706,999 B2 | 7/2017 | Motai |
| 9,713,469 B2 | 7/2017 | Leimbach et al. |
| 9,737,304 B2 | 8/2017 | Bettuchi et al. |
| 9,743,955 B2 | 8/2017 | Hill et al. |
| 9,750,503 B2 | 9/2017 | Milliman |
| 9,763,663 B2 | 9/2017 | Weisshaupt et al. |
| 9,801,626 B2 | 10/2017 | Parihar et al. |
| 9,833,235 B2 | 12/2017 | Penna et al. |
| 9,844,368 B2 | 12/2017 | Boudreaux et al. |
| 9,861,368 B2 | 1/2018 | Racenet et al. |
| 9,883,862 B2 | 2/2018 | Rebuffat et al. |
| 9,907,600 B2 | 3/2018 | Stulen et al. |
| 10,039,549 B2 | 8/2018 | Williams |
| 10,085,744 B2 | 10/2018 | Williams et al. |
| 10,105,137 B2 | 10/2018 | Holsten et al. |
| 10,117,655 B2 | 11/2018 | Scirica et al. |
| 10,117,656 B2 | 11/2018 | Sgroi, Jr. |
| 10,136,888 B2 | 11/2018 | Chen et al. |
| 10,149,680 B2 | 12/2018 | Parihar et al. |
| 10,154,845 B2 | 12/2018 | Williams |
| 10,172,622 B2 | 1/2019 | Kelley |
| 10,178,994 B2 | 1/2019 | Lee et al. |
| 10,188,386 B2 | 1/2019 | Measamer et al. |
| 10,190,888 B2 | 1/2019 | Hryb et al. |
| 10,194,911 B2 | 2/2019 | Miller et al. |
| 10,226,253 B2 | 3/2019 | DiNardo et al. |
| 10,245,038 B2 | 4/2019 | Hopkins et al. |
| 10,271,842 B2 | 4/2019 | Fox et al. |
| 10,271,843 B2 | 4/2019 | Shi et al. |
| 10,307,157 B2 | 6/2019 | Miller et al. |
| 10,321,908 B2 | 6/2019 | Carter et al. |
| 10,327,779 B2 | 6/2019 | Richard et al. |
| 10,342,629 B2 | 7/2019 | Penna et al. |
| 10,405,855 B2 | 9/2019 | Stager et al. |
| 10,413,299 B2 | 9/2019 | Milliman |
| 10,426,468 B2 | 10/2019 | Contini et al. |
| 10,426,480 B2 | 10/2019 | Scirica et al. |
| 10,433,848 B2 | 10/2019 | Chen et al. |
| 10,456,134 B2 | 10/2019 | DiNardo et al. |
| 10,463,365 B2 | 11/2019 | Williams |
| 10,463,373 B2 | 11/2019 | Mozdzierz et al. |
| 10,463,374 B2 | 11/2019 | Sgroi, Jr. |
| 10,470,770 B2 | 11/2019 | Shelton, IV et al. |
| 10,470,771 B2 | 11/2019 | D'Agostino et al. |
| 10,499,922 B2 | 12/2019 | Sgroi, Jr. |
| 10,506,920 B2 | 12/2019 | Hasser et al. |
| 10,507,039 B2 | 12/2019 | Williams |
| 10,512,467 B2 | 12/2019 | Swayze et al. |
| 10,524,795 B2 | 1/2020 | Nalagatla et al. |
| 10,524,798 B2 | 1/2020 | Williams |
| 10,524,868 B2 | 1/2020 | Cooper et al. |
| 10,537,331 B2 | 1/2020 | Scirica et al. |
| 10,542,993 B2 | 1/2020 | Guerrera et al. |
| 10,548,598 B2 | 2/2020 | Prescott et al. |
| 10,561,424 B2 | 2/2020 | Penna et al. |
| 10,568,631 B2 | 2/2020 | Rebuffat et al. |
| 10,575,847 B2 | 3/2020 | Hessler et al. |
| 10,595,871 B2 | 3/2020 | Racenet et al. |
| 10,595,872 B2 | 3/2020 | Milliman |
| 10,603,042 B2 | 3/2020 | Sgroi |
| 10,624,646 B2 | 4/2020 | Bae et al. |
| 10,639,041 B2 | 5/2020 | Williams |
| 10,653,414 B2 | 5/2020 | Williams |
| 10,898,196 B2 | 1/2021 | Sapienza et al. |
| 2002/0095175 A1 | 7/2002 | Brock et al. |
| 2002/0117534 A1 | 8/2002 | Green et al. |
| 2003/0111507 A1 | 6/2003 | Nunez |
| 2004/0094597 A1 | 5/2004 | Whitman et al. |
| 2004/0236192 A1 | 11/2004 | Necola Shehada et al. |
| 2004/0243207 A1 | 12/2004 | Olson et al. |
| 2005/0004478 A1 | 1/2005 | Fitz |
| 2005/0051597 A1 | 3/2005 | Toledano |
| 2005/0107813 A1 | 5/2005 | Gilete Garcia |
| 2005/0131390 A1 | 6/2005 | Heinrich et al. |
| 2005/0158360 A1 | 7/2005 | Falotico et al. |
| 2005/0165317 A1 | 7/2005 | Turner et al. |
| 2005/0173490 A1 | 8/2005 | Shelton |
| 2006/0000869 A1 | 1/2006 | Fontayne |
| 2006/0011698 A1 | 1/2006 | Okada et al. |
| 2006/0089547 A1 | 4/2006 | Sarussi |
| 2006/0200012 A1 | 9/2006 | Mansour et al. |
| 2006/0200220 A1 | 9/2006 | Brown et al. |
| 2006/0201989 A1 | 9/2006 | Ojeda |
| 2006/0212069 A1 | 9/2006 | Shelton |
| 2007/0027371 A1 | 2/2007 | Benaron et al. |
| 2007/0027473 A1 | 2/2007 | Vresh et al. |
| 2007/0029363 A1 | 2/2007 | Popov |
| 2007/0060952 A1 | 3/2007 | Roby et al. |
| 2007/0084896 A1 | 4/2007 | Doll et al. |
| 2008/0033273 A1 | 2/2008 | Zhou et al. |
| 2008/0058652 A1 | 3/2008 | Payne |
| 2008/0108885 A1 | 5/2008 | Colvin |
| 2008/0149685 A1 | 6/2008 | Smith et al. |
| 2008/0154101 A1 | 6/2008 | Jain et al. |
| 2008/0154288 A1 | 6/2008 | Belson |
| 2008/0287788 A1 | 11/2008 | Richardson et al. |
| 2009/0001128 A1 | 1/2009 | Weisenburgh, II et al. |
| 2009/0054908 A1 | 2/2009 | Zand et al. |
| 2009/0114701 A1 | 5/2009 | Zemlok et al. |
| 2009/0130021 A1 | 5/2009 | Munch et al. |

(56) References Cited

U.S. PATENT DOCUMENTS

| | | |
|---|---|---|
| 2009/0134200 A1 | 5/2009 | Tarinelli et al. |
| 2009/0163782 A1 | 6/2009 | Shehada et al. |
| 2009/0212088 A1 | 8/2009 | Okada et al. |
| 2009/0234248 A1 | 9/2009 | Zand et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2009/0299153 A1 | 12/2009 | Gerber et al. |
| 2010/0019016 A1 | 1/2010 | Edoga et al. |
| 2010/0051668 A1 | 3/2010 | Milliman et al. |
| 2010/0081895 A1 | 4/2010 | Zand |
| 2010/0084453 A1 | 4/2010 | Hu |
| 2010/0106194 A1 | 4/2010 | Bonutti et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2011/0011916 A1 | 1/2011 | Levine |
| 2011/0017801 A1 | 1/2011 | Zemlok et al. |
| 2011/0114697 A1 | 5/2011 | Baxte, III et al. |
| 2011/0114700 A1 | 5/2011 | Baxter, III et al. |
| 2011/0144640 A1 | 6/2011 | Heinrich et al. |
| 2011/0192882 A1 | 8/2011 | Hess et al. |
| 2012/0012638 A1* | 1/2012 | Huang ............... A61B 17/1114 227/176.1 |
| 2012/0116416 A1 | 5/2012 | Neff et al. |
| 2012/0145755 A1 | 6/2012 | Kahn |
| 2012/0193395 A1 | 8/2012 | Pastorelli et al. |
| 2012/0193396 A1 | 8/2012 | Zemlok et al. |
| 2012/0193398 A1 | 8/2012 | Williams et al. |
| 2012/0232339 A1 | 9/2012 | Csiky |
| 2012/0273548 A1* | 11/2012 | Ma ....................... A61B 5/7405 227/176.1 |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0060258 A1 | 3/2013 | Giacomantonio |
| 2013/0105544 A1 | 5/2013 | Mozdzierz et al. |
| 2013/0105551 A1 | 5/2013 | Zingman |
| 2013/0126580 A1 | 5/2013 | Smith et al. |
| 2013/0153631 A1 | 6/2013 | Vasudevan et al. |
| 2013/0172717 A1 | 7/2013 | Halpern et al. |
| 2013/0175315 A1 | 7/2013 | Milliman |
| 2013/0175318 A1 | 7/2013 | Felder et al. |
| 2013/0181035 A1 | 7/2013 | Milliman |
| 2013/0181036 A1 | 7/2013 | Olson et al. |
| 2013/0193190 A1 | 8/2013 | Carter et al. |
| 2013/0200131 A1 | 8/2013 | Racenet et al. |
| 2013/0206816 A1 | 8/2013 | Penna |
| 2013/0240597 A1 | 9/2013 | Milliman et al. |
| 2013/0277411 A1 | 10/2013 | Hodgkinson et al. |
| 2013/0284792 A1 | 10/2013 | Ma |
| 2013/0289367 A1 | 10/2013 | Kruglick et al. |
| 2014/0008413 A1 | 1/2014 | Williams |
| 2014/0046352 A1 | 2/2014 | Reboa et al. |
| 2014/0158747 A1 | 6/2014 | Measamer et al. |
| 2014/0284370 A1 | 9/2014 | Sahin |
| 2015/0083772 A1 | 3/2015 | Miller et al. |
| 2015/0173763 A1 | 6/2015 | Liu |
| 2015/0209045 A1 | 7/2015 | Hodgkinson et al. |

FOREIGN PATENT DOCUMENTS

| | | | |
|---|---|---|---|
| CN | 104039244 A | 9/2014 | |
| CN | 104042288 A | 9/2014 | |
| CN | 104367360 A | 2/2015 | |
| DE | 1057729 B | 5/1959 | |
| DE | 3301713 A1 | 7/1984 | |
| EP | 0152382 A2 | 8/1985 | |
| EP | 0173451 A1 | 3/1986 | |
| EP | 0190022 A2 | 8/1986 | |
| EP | 0282157 A1 | 9/1988 | |
| EP | 0503689 A2 | 9/1992 | |
| EP | 1354560 A2 | 10/2003 | |
| EP | 1671597 A1 | 6/2006 | |
| EP | 2138118 A2 | 12/2009 | |
| EP | 2168510 A1 | 3/2010 | |
| EP | 2238926 A2 | 10/2010 | |
| EP | 2524656 A2 | 11/2012 | |
| EP | 3023077 A1 | 5/2016 | |
| EP | 3381380 A2 | 10/2018 | |
| EP | 3412225 A1 | 12/2018 | |
| EP | 3506274 A1 * | 7/2019 | ............ A61B 17/072 |
| EP | 3549545 A2 | 10/2019 | |
| FR | 1136020 A | 5/1957 | |
| FR | 1461464 A | 2/1966 | |
| FR | 1588250 A | 4/1970 | |
| FR | 2443239 A1 | 7/1980 | |
| GB | 1185292 A | 3/1970 | |
| GB | 2016991 A | 9/1979 | |
| GB | 2070499 A | 9/1981 | |
| JP | 2004147969 A | 5/2004 | |
| JP | 2013138860 A | 7/2013 | |
| NL | 7711347 A | 4/1979 | |
| SU | 1509052 A1 | 9/1989 | |
| WO | 8706448 A1 | 11/1987 | |
| WO | 8900406 A1 | 1/1989 | |
| WO | 9006085 A1 | 6/1990 | |
| WO | 9835614 A1 | 8/1998 | |
| WO | 0154594 A1 | 8/2001 | |
| WO | 02080781 A2 | 10/2002 | |
| WO | 2004047654 A2 | 6/2004 | |
| WO | 2008107918 A1 | 9/2008 | |
| WO | 2019130087 A1 | 7/2019 | |
| WO | 2020021433 A1 | 1/2020 | |

OTHER PUBLICATIONS

Extended European Search Report from Appl. No. 14181908.6 dated May 26, 2015.

European Examination Report from Appl. No. 14181908.6 dated May 3, 2016.

Australian Examination Report dated Apr. 16, 2013 in corresponding Australian Application No. 2012202180.

* cited by examiner

SYSTEMS AND METHODS FOR POST-OPERATIVE ANASTOMOTIC LEAK DETECTION

FIELD

This disclosure relates generally to systems and methods for tissue monitoring after a surgical procedure. In particular, this disclosure relates to systems and methods for monitoring an anastomosis for early detection of anastomotic leakage.

BACKGROUND

Colectomy procedures are performed in patients with, for example, cancer, diverticulitis, trauma, and inflammatory bowel disease. Following surgery on the gastrointestinal system, in which a portion of the large intestine is removed and the large intestine undergoes anastomosis, there is an incidence of subsequent leakage from the large intestine into the peritoneal cavity. Anastomotic leakage can occur in about 4-9% of patients, depending upon the colorectal procedure, with the highest percentages associated with low anterior resection. This complication can have serious consequences for the patient, such as peritonitis, that affects the patient's prognosis, impacts the cost of treatment, and prolongs the hospital stay.

Anastomotic leak detection is generally accomplished by monitoring clinical signs of infection, including white blood cell count, fever, malaise, heart rate, etc. A recognized problem of using clinical signs is that there is a lag between the time the leak occurs and the onset of signs or symptoms. This results in the severity of the problem escalating prior to its detection and the appropriate treatment being instituted.

Imaging modalities, such as fluoroscopy, may be utilized to monitor for anastomotic leakage after administering radiopaque dye orally or rectally. Imaging modalities, however, have limitations of sensitivity and specificity, and require significant resources and cost to perform. Additional anastomotic leak detection attempts of measuring effluent from drains have demonstrated some success. Limitations of this approach, however, include the inconsistent use of drains due to concomitant complications (e.g., infection, clogging, migration, etc.) and identification of markers from drain fluid may be delayed after the leak occurs.

SUMMARY

This disclosure generally relates to systems and methods for monitoring an anastomosis for acute stage detection of complications associated with the anastomosis thereby enabling early intervention for improved patient outcomes. The systems and methods help detect complications at an early onset (e.g., detecting local infection at the anastomotic site) before the onset of symptoms from systemic infection, thereby enabling a physician to evaluate predictors of morbidity and intervene to minimize severe adverse effects associated with the complication and reduce patient suffering, medical costs associated with treatment, and the length of the hospital stay.

The systems of this disclosure automatically monitor patients post-operatively thereby having direct clinical impact on improving patient recovery and reducing hospital costs. Further, because the systems collect post-surgery physiological data, the physiological data may be aggregated from systems and further used and processed in data analytic scenarios for surgical device and procedure optimization.

In one aspect, the disclosure provides an end effector for a surgical device including a loading unit having a staple cartridge including staple pockets defined therein and staples disposed within the staple pockets. The loading unit includes a sensor assembly coupled to one of the staples. The sensor assembly includes a sensor and a tether interconnecting the sensor and the respective staple.

In aspects, the staple cartridge has an annular configuration including an outer side wall and an inner side wall defining a central aperture therethrough. In some aspects, the sensor of the sensory assembly is disposed within the central aperture of the staple cartridge. In some aspects, the loading unit further includes a knife disposed within the central aperture of the staple cartridge, and the sensor is positioned between the inner side wall of the staple cartridge and an outer wall of the knife. In certain aspects, the staple cartridge includes a tissue facing surface extending across a distal end of the staple cartridge between the outer and inner side walls, and the tether of the sensor assembly extends out of the respective staple pocket, across a portion of the tissue facing surface, and into the central aperture.

In some aspects, the loading unit further includes a housing in which the staple cartridge is positioned, and the sensor of the sensor assembly is disposed against an outer wall of the housing. In certain aspects, the staple cartridge includes a tissue facing surface extending across a distal end of the staple cartridge between the outer and inner side walls, and the tether of the sensor assembly extends out of the respective staple pocket, across a portion of the tissue facing surface, and over an outer edge of the staple cartridge.

In aspects, the tether of the sensor assembly is formed from a bioabsorbable material. In aspects, the sensor is a temperature sensor.

In aspects, the sensor assembly further includes an annular band coupled to the sensor. In some aspects, the annular band is positioned against the inner side wall of the staple cartridge. In some aspects, the loading unit further includes a housing in which the staple cartridge is positioned, and the annular band is positioned around an outer wall of the housing.

In another aspect, the disclosure provides a method of monitoring tissue which includes implanting a sensor into tissue. The sensor is coupled to a staple by a tether and is configured to measure a physiological parameter of the tissue. The method further includes monitoring the physiological parameter of the tissue on a computing device via information transmitted from the sensor to the computing device by a sensor reader.

In aspects, implanting the sensor includes stapling the staple to the tissue.

In yet another aspect, the disclosure provides a tissue monitoring system including a sensor, a sensor reader, and at least one computing device. The sensor is releasably coupled to a staple by a tether and is configured to measure a physiological parameter of tissue and convert the measurement into a signal. The sensor reader is configured to receive the signal from the sensor, and the at least one computing device is configured to receive the signal from the sensor reader and process the signal into physiological data.

In aspects, the at least one computing device includes a display for displaying the physiological data.

In some aspects, the sensor reader is sized and shaped to be worn on a body of a patient and, in some other aspects, the sensor reader is integrated into the at least one computing device.

In aspects, the tissue monitoring system further includes a server configured to store and process the physiological data. In some aspects, the tissue monitoring system further includes a network through which signals are sent and received between the at least one computing device and the server.

The details of one or more aspects of the disclosure are set forth in the accompanying drawings and the description below. Other features, objects, and advantages of the aspects described in this disclosure will be apparent from the description and drawings, and from the claims.

BRIEF DESCRIPTION OF THE DRAWINGS

Various aspects of this disclosure are described hereinbelow with reference to the drawings, which are incorporated in and constitute a part of this specification, wherein.

DETAILED DESCRIPTION

Figure 1:
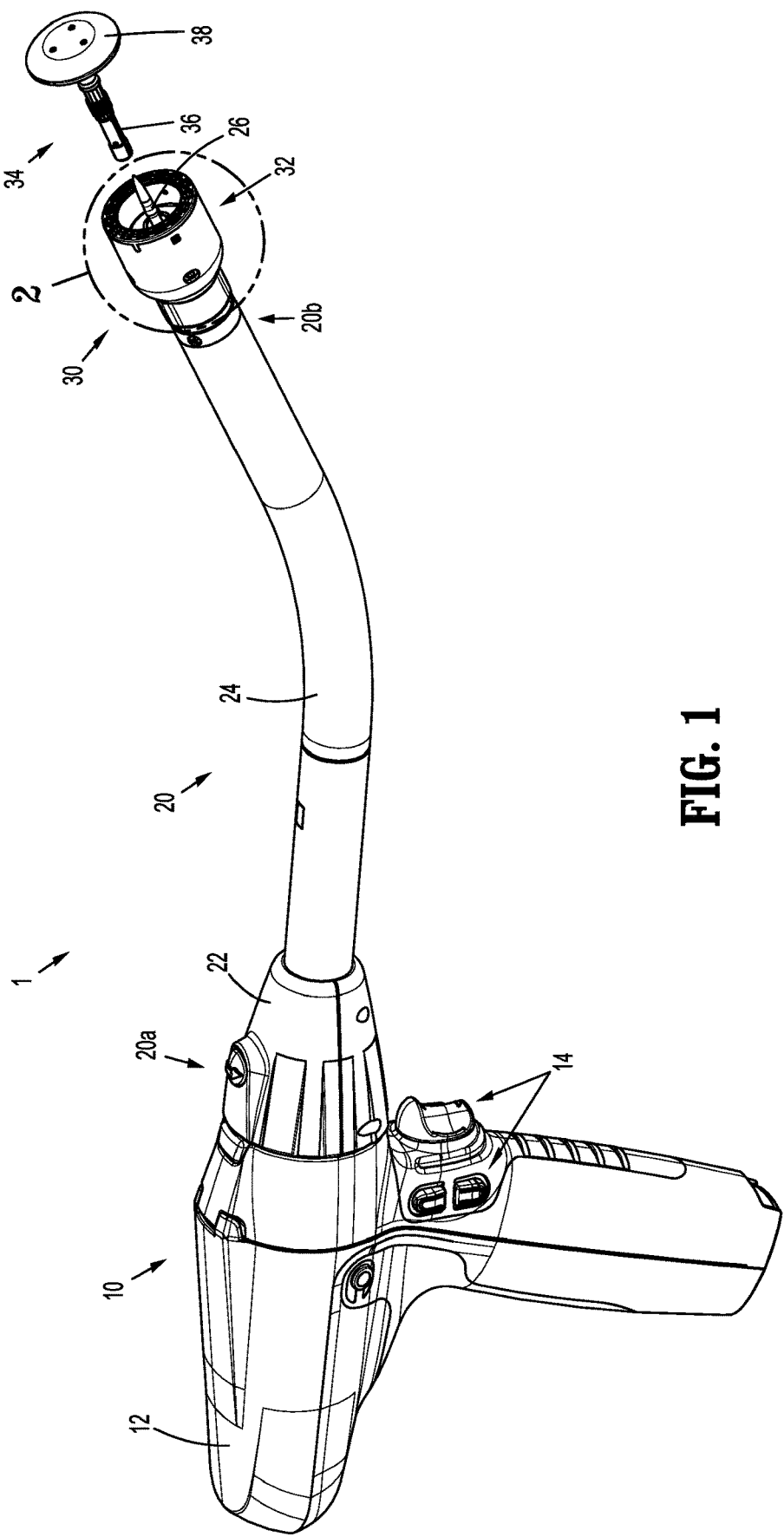
FIG. 1 is a perspective view of a surgical device in accordance with aspects of the disclosure.

Aspects of this disclosure are described hereinbelow with reference to the accompanying drawings; however, it is to be understood that the disclosed aspects are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

Like reference numerals refer to similar or identical elements throughout the description of the figures. It should be understood that various elements of the disclosure, such as those plainly numbered, correspond to elements of the disclosure similarly prime numbered, such that redundant explanation of similar elements need not be repeated herein. Throughout this description, the term "proximal" refers to a portion of a structure, or component thereof, that is closer to a clinician, and the term "distal" refers to a portion of the structure, or component thereof, that is farther from the clinician. As used herein, the term "patient" should be understood as referring to a human subject or other animal, and the term "clinician" should be understood as referring to a doctor, nurse, or other care provider and may include support personnel.

Turning now to FIG. 1, a surgical device 1, in accordance with an aspect of this disclosure, is in the form of a powered handheld electromechanical instrument. The surgical device 1 includes a powered handle assembly 10, an adapter assembly 20, and a tool assembly or end effector 30 including a loading unit 32 and an anvil assembly 34. The powered handle assembly 10 is configured for selective connection with the adapter assembly 20 and, in turn, the adapter assembly 20 is configured for selective connection with the end effector 30.

The surgical device 1 will further be described to the extent necessary to disclose aspects of the disclosure. For a detailed description of the structure and function of exemplary surgical devices, reference may be made to U.S. Pat. Nos. 10,327,779 and 10,426,468, the entire contents of each of which are incorporated herein by reference.

With continued reference to FIG. 1, the powered handle assembly 10 includes a handle housing 12 housing a power-pack (not shown) configured to power and control various operations of the surgical device 1, and a plurality of actuators 14 (e.g., finger-actuated control buttons, knobs, toggles, slides, interfaces, and the like) for activating various functions of the surgical device 1 (e.g., approximating the anvil assembly 34 towards the loading unit 32, firing staples 60 (FIG. 3) from the loading unit 32, cutting tissue secured between the loading unit 32 and the anvil assembly 34, etc.).

The adapter assembly 20 has a proximal portion 20a including a knob housing 22 configured for operable connection to the handle assembly 10 and an elongate tubular body 24 extending distally from the knob housing 22 that is configured for operable connection to the end effector 30. The elongate tubular body 24 may be flexible or rigid, and/or straight or curved along a portion of the entirety thereof. The adapter assembly 20 is configured to enable communication between the handle assembly 10 and the end effector 30 and to relay power from the handle assembly 10 to the end effector 30.

The loading unit 32 of the end effector 30 is operably mounted and releasably coupled to a distal portion 20b of the adapter assembly 20. The loading unit 32 may be configured to concentrically fit within, or be otherwise connected, to the distal portion 20b of the adapter assembly 20 such that the loading unit 32 is removable and replaceable. The loading unit 32 is a disposable loading unit ("DLU") that is releasably secured to the elongate tubular body 24 and thus, replaceable with a new loading unit 32. The loading unit 32 may be a single use loading unit ("SULU") that is used one time and then replaced. For example, during a surgical procedure, the surgical device 1 can be used to staple and cut tissue, and the entire SULU is replaced after each staple and cut operation of the surgical device 1. The loading unit 32 may be a multi-use loading unit ("MULU") that is re-useable a predetermined number of times. For example, during a surgical procedure, the surgical device 1 can be used to staple and cut tissue, and a reload assembly (e.g., a staple cartridge 42 as seen in FIG. 2) of the MULU is replaced after each staple and cut operation of the surgical device 1 a pre-determined number of times before the entire MULU needs to be replaced.

The anvil assembly 34 includes an anvil rod 36 and an anvil head 38 extending distally from the anvil rod 36. The anvil rod 36 is releasably connectable to the distal portion 20b of the adapter assembly 20. The anvil rod 36 may be connected to a trocar assembly 26, which extends through and is longitudinally movable relative to the elongate tubular body 24, to move the anvil assembly 34 away from the elongate tubular body 24 (e.g., to an open position), allowing tissue to be placed or released from between the anvil assembly 34 and the loading unit 32, and towards the elongate tubular body 24 (e.g., to a closed or approximated position), allowing tissue to be secured (e.g., clamped) between the anvil assembly 34 and the loading unit 32.

Figure 2:
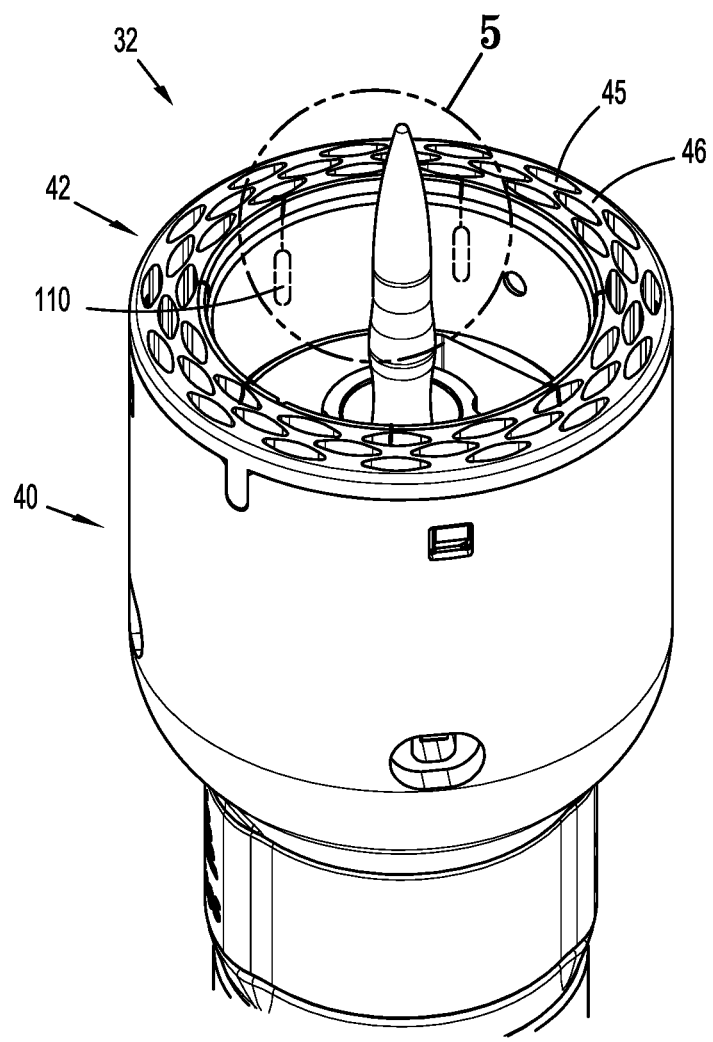
FIG. 2 is a perspective view of a loading unit of the surgical device of FIG. 1.
Figure 3:
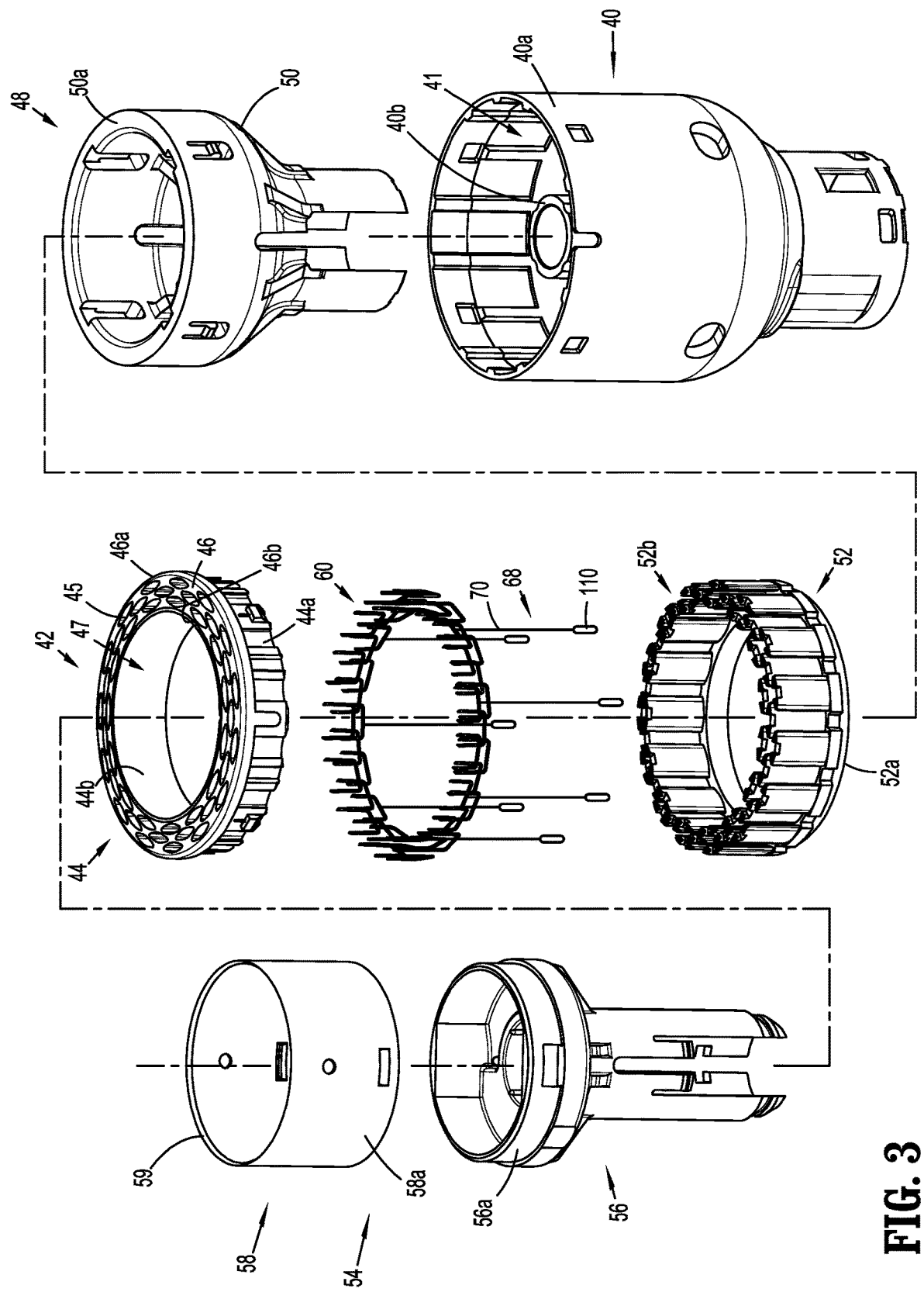
FIG. 3 is a perspective view, with parts separated, of the loading unit of FIG. 2.

With reference now to FIGS. 2 and 3, the loading unit 32 includes a housing 40, a staple cartridge 42, a staple pusher assembly 48, and a knife assembly 54. The housing 40 includes an outer cylindrical portion 40a and an inner cylindrical portion 40b. The outer and inner cylindrical portions 40a, 40b are coaxial and define an annular cavity 41 therebetween configured to receive the staple pusher assembly 48 and the knife assembly 54 therein.

The staple cartridge 42 includes a cartridge body 44 and staples 60 supported within staple pockets 45 defined in the cartridge body 44. The cartridge body 44 has an annular configuration and defines a central aperture 47 therethrough. The cartridge body 44 includes an outer side wall 44a, an inner side wall 44b, and a tissue facing surface 46 extending across a distal end of the cartridge body 44 between the outer and inner side walls 44a, 44b. The tissue facing surface 46 has an outer edge 46a and an inner edge 46b. The staple pockets 45 extend through and are open at the tissue facing surface 46 for deployment of the staples 60 therethrough. The staple cartridge 42 is positioned within the housing 40 of the loading unit 32 such that the tissue facing surface 46 is disposed at a distal end of the loading unit 32.

Each of the staple pockets 45 houses one of the staples 60 therein. While the staple cartridge 44 is shown as including three annular rows of staple pockets 45, it should be understood that the staple cartridge 44 may include one or more rows, or partial rows, of staple pockets 45 in a variety of arrangements. It should further be understood that the shape of the staple pockets 45 may vary (e.g., the staple pockets may have a curved or angled shape) to accommodate the positioning of the staples 60 relative to each other, and/or the size of the staple pockets 45 may vary (e.g., one or more rows of staple pockets may be different in size from other row(s) of staple pockets) to accommodate different shaped and/or sized staples 60.

The staple pusher assembly 48 includes a staple pusher actuator 50 and a staple pusher 52 supported by the staple pusher actuator 50. The staple pusher actuator 50 is supported within the housing 40 and is longitudinally movable therein between a retracted position and an advanced position. The staple pusher actuator 50 includes an annular distal end 50a that engages an annular proximal end 52a of the staple pusher 52. The staple pusher 52 has fingers 52b extending distally therefrom, with each finger 52b received within a respective one of the staple pockets 45 of the staple cartridge 42. The fingers 52b are movable through the respective staple pocket 45 to eject the staples 60 from the staple pockets 45 when the staple pusher actuator 50 is moved distally within the housing 40 from the retracted position to the advanced position.

The knife assembly 54 includes a knife pusher 56 and a knife 58 supported by the knife pusher 56. The knife pusher 56 is supported within the housing 40 and is longitudinally movable therein between a retracted position and an advanced position. The knife pusher 56 includes an annular distal end portion 56a that engages an annular proximal end portion 58a of the knife 58. The knife 58 has a cylindrical shape with a distal rim defining a knife blade 59. The knife assembly 54 is disposed radially inwardly of the staple pusher assembly 48 so that, in use, as the staple pusher assembly 48 is advanced distally (e.g., axially outwardly) from the retracted position to the advanced position, the knife assembly 54 is also advanced distally such that the staples 60 are driven through tissue captured between the loading unit 32 and the anvil assembly 34 (FIG. 1), and portions of the tissue disposed radially inwardly of the staples 60 are cut by the knife blade 59.

Figure 4:
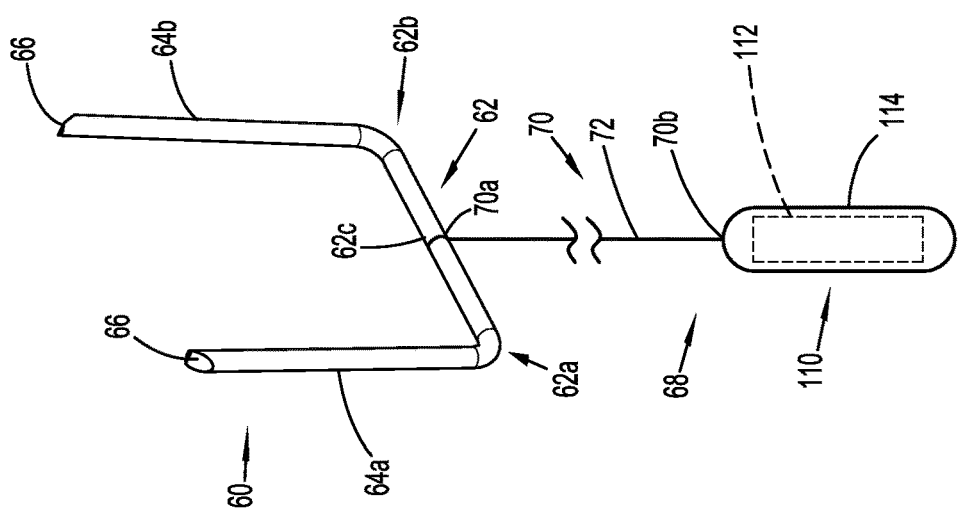
FIG. 4 is a perspective view of a staple disposed within the loading unit of FIG. 2, the staple having a sensor assembly coupled thereto.

With continued reference to FIG. 3, in conjunction with FIG. 4, each of the staples 60 includes a backspan or crown 62, a first leg 64a extending from a first end 62a of the backspan 62, and a second leg 64b extending from a second end 62b of the backspan 62. The first and second legs 64a, 64b terminate at tissue penetrating tips 66. The staples 60 are fabricated from a biocompatible material which is bioabsorbable or non-absorbable, natural or synthetic, or any combination thereof. The staples may be formed, for example from a metal (e.g., titanium or stainless steel) or a polymer.

The first and second legs 64a, 64b of the staple 60 extend in the same direction from the backspan 62 and are substantially parallel when in an unformed condition (e.g., having a U-like configuration). The first and second legs 64a, 64b are bent towards each other and the backspace 62 when in a formed condition (e.g., having a B-like configuration). In this manner, the staples 60 are introduced into tissue while in the unformed condition and then are formed or fastened onto the tissue to secure the staples thereto. It should be understood that the staples 60 may have other configurations, as is within the purview of those skilled in the art. Additionally, it should be understood that other types of tissue fasteners (e.g., clips, tacks, etc.) may be utilized with aspects of the disclosure.

As further seen in FIGS. 3 and 4, a pre-determined number of the staples 60 disposed within the staple cartridge 42 include a sensor assembly 68 associated therewith. The sensor assembly 68 includes a tether 70 and a sensor 110. As specifically seen in FIG. 4, the sensor 110 is coupled to the staple 60 by the tether 70. The tether 70 includes a flexible elongate body 72 utilized as a leash for releasably securing the sensor 110 to the staple 60. In aspects, the tether 70 is a suture. The tether 70 is formed from a biocompatible, bioabsorbable or bioresorable material. In aspects, the tether 70 is biodegradable such that the tether 70 decomposes or is broken down (physically or chemically) under physiological conditions in the body, and the degradation products are excretable or absorbable by the body. The tether 70 is designed to break down after a pre-determined period of time associated with the desired monitoring period of the sensors 110 such that after tissue monitoring is complete, the sensors 110 are released from a patient's body (e.g., about 7 days).

The tether 70 has a first end portion 70a coupled (e.g., secured) to the staple 60 and a second end portion 70b coupled (e.g., secured) to the sensor 110. In aspects, the first end portion 70a of the tether 70 is coupled to the backspan 62 of the staple 60 and, in some aspects, the first end portion 70a of the tether 70 is coupled to a center 62c of the backspan 62. It is envisioned that the first end portion 70a of the tether 70 may be coupled to any portion of the staple 60. The tether 70 may be secured to the staple 60 by, for example, tying the first end portion 70a of the tether 70 around the staple 60, welding the first end portion 70a of the tether 70 to the staple 60, utilizing adhesives or coatings to secure the first end portion 70a of the tether 70 to the staple 60, among other techniques within the purview of those skilled in the art. The second end portion 70b of the tether 70 may be similarly secured to the sensor 110.

The sensor 110 includes a sensing assembly 112 (shown in phantom) disposed within a housing 114 (e.g., a capsule). In aspects, the sensing assembly 112 is an electronics assembly (e.g., a microchip) configured to measure a physiological parameter or property of the tissue or tissue environment in which the sensor 110 is placed and, in some aspects, is programmed to include patient identifying information. The sensing assembly 112 converts the measurement into a signal which is transmitted to a sensor reader 120 (FIG. 10), as described in further detail below. The sensor 110 is wireless such that the signals are sent via a wireless communication link to the sensor reader 120. In aspects, the sensor 110 is a transponder that is battery free and powered or scanned externally by the sensor reader 120 (e.g., by inductance, such as inductive telemetry) to take readings continuously, periodically (e.g., at scheduled intervals), or when requested. In such aspects, issues associated with battery leakage, encapsulation and retraction of embedded wires, among other issues within the purview of those skilled in the art are eliminated.

The housing 114 of the sensor 110 is formed from a biocompatible material that has suitable physical properties for the intended use in vivo. The biocompatible material should be non-fouling and non-damaging to surrounding tissue, and resistant to device-related infection. In aspects, the housing 114 is fabricated from a material which will not trigger a fibrotic response over the term of use such that the sensor 110 may be placed, e.g., made indwelling, in a temporary fashion adjacent a tissue of interest in a location which allows the sensor 110 to detect the physiological parameter of interest. The housing 114 may be formed from a polymer (e.g., polycarbonate, polyethyelene, or polysiloxane) and, in some aspects, is transparent or translucent. As an alternative to the housing 114, the sensor 110 may include a biocompatible coating encapsulating the sensing assembly 112.

The sensor 110 may be any type of sensor within the purview of those skilled in the art for measuring and/or identifying a physiological condition or state related to complications that may arise post-surgery (e.g., tissue perfusion, tissue ischemia and/or reperfusion, pH, bacterial load, temperature, among other physiological parameters of interest). The sensor 110 may be, for example, an optical sensor, an electrical sensor, a biochemical sensor, an acoustic sensor, a light sensor, etc. The sensors 110 disposed within the loading unit 32 (FIG. 2) may all be the same, or different sensors may be utilized to monitor the same or different physiological parameter(s). In aspects, the sensors 110 are temperature sensors. Without being bound to any particular theory, local temperature rise at the genesis of infection has been shown to precede systemic infection. Accordingly, the temperature at the boundaries of an anastomosis can be monitored by the sensors 110 for the onset of infection caused, for example, by anastomotic leakage.

Figure 5:
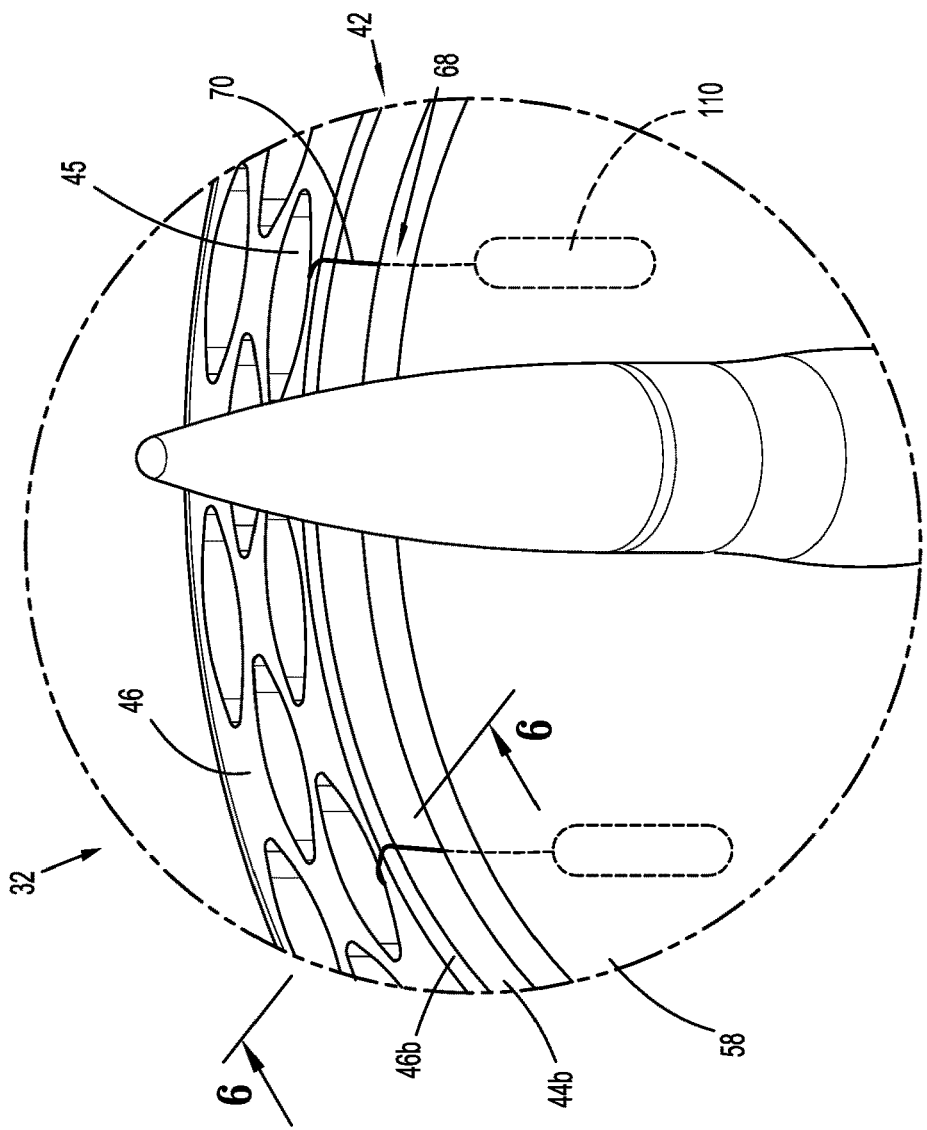
FIG. 5 is a close-up view of the area of detail 5 indicated in FIG. 2, showing the sensor assembly of FIG. 4 within the loading unit of FIG. 2.
Figure 6:
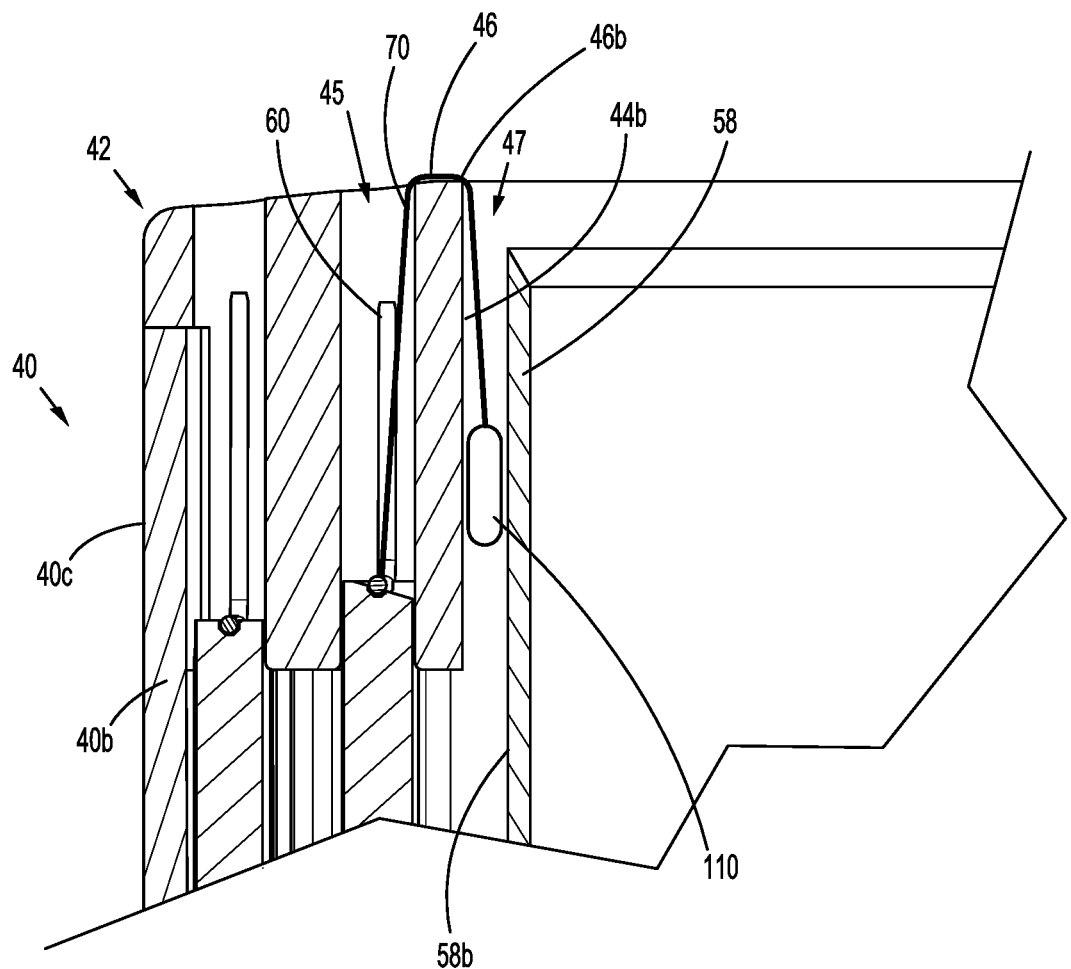
FIG. 6 is a partial cross-sectional view of the loading unit of FIG. 5, take along section line 6-6 of FIG. 5.

As shown in FIGS. 5 and 6, the staples 60 are disposed within the staple pockets 45 of the staple cartridge 42, and the sensors 110 are disposed between the inner side wall 44b of the staple cartridge 42 and an outer wall 58b of the knife 58. As specifically shown in FIG. 6, the tether 70 extends out of the staple pocket 45, across the tissue facing surface 46, over the inner edge 46b, and into the central aperture 47 of the staple cartridge 42 radially outwardly of the knife 58.

While the sensor assemblies 68 are all associated with staples 60 disposed within an innermost annular row of the staple pockets 45, it should be understood that the sensor assemblies 68 may be associated with staples 60 disposed in any of the staple pockets 45 (e.g., in a middle or outer annular row), and the length of the tethers 70 are adjusted accordingly to retain the position of the sensors 110 between the staple cartridge 42 and the knife 58. Further, while the sensors 110 are shown in a configuration that are evenly spaced relative to each other around the knife 58, it should be understood that the number, position, and/or pattern of the sensors 110 may vary depending upon the desired functionality once implanted into tissue, as is within the purview of those skilled in the art. Further still, while the sensors 110 are shown disposed adjacent to the inner side wall 44b of the staple cartridge 42, it should be understood that the sensors 110 may be otherwise positioned.

Figure 7:
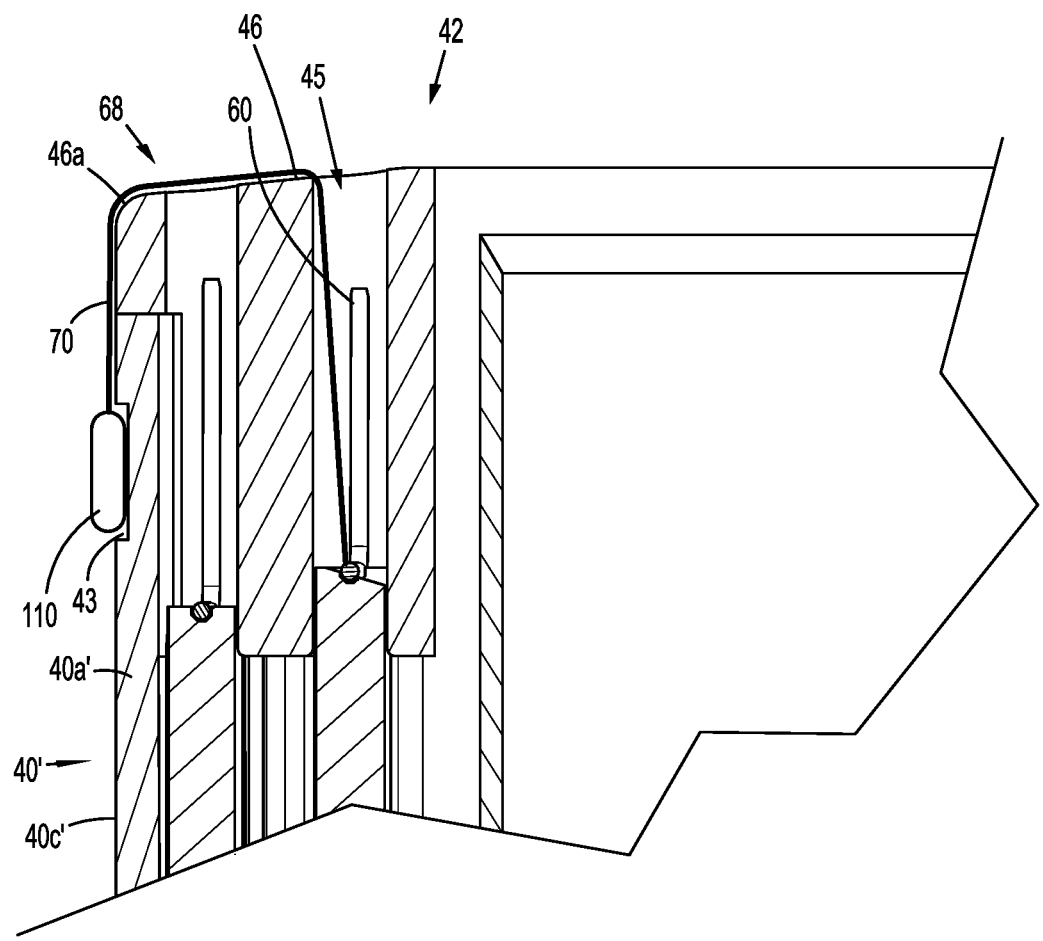
FIG. 7 is a partial cross-sectional view of a loading unit in accordance with another aspect of the disclosure.

For example, as shown in FIG. 7, staples 60, which include the sensor assemblies 68, are disposed in a middle annular row of the staple pockets 45 of the staple cartridge 42. The tethers 70 extend out of the staple pockets 45, across the tissue facing surface 46, and over the outer edge 46a of the staple cartridge 42 such that the sensors 110 are positioned adjacent to an outer wall 40c' of the housing 40'. In aspects, the sensors 110 are temporarily secured to the outer wall 40c' by utilizing an adhesive or coating (e.g., a water-soluble coating), or a tape that is removed prior to use. In some aspects, the outer wall 40c' of the housing 40' includes one or more grooves 43 defined therein in which the sensors 110 are positioned.

Figure 8:
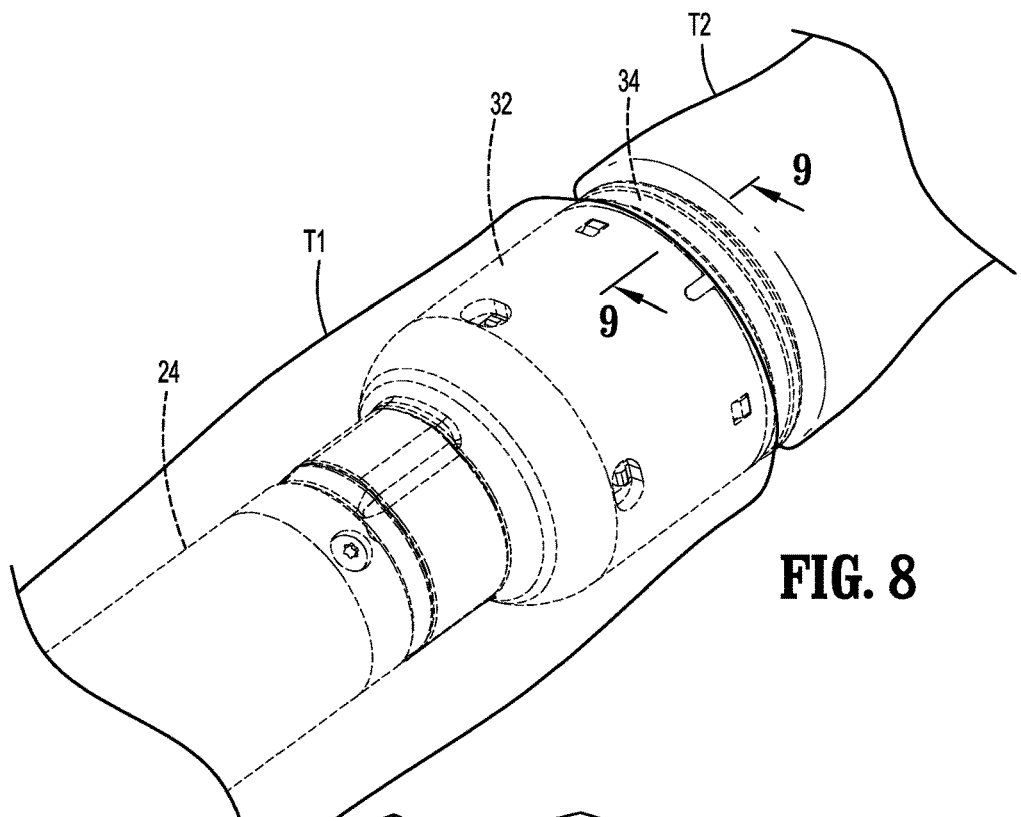
FIG. 8 is a perspective view of an end effector of the surgical device of FIG. 1 including the loading unit of FIG. 2, shown positioned within tissue during a firing stroke of the surgical device.
Figure 9:
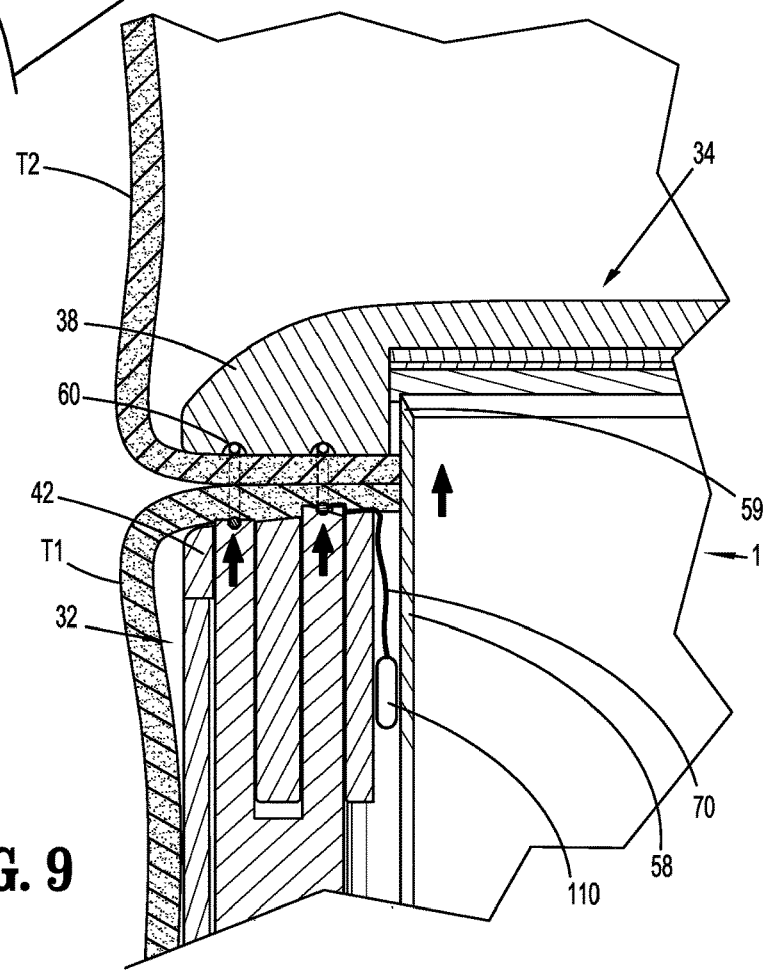
FIG. 9 is a cross-sectional view of the tissue and the end effector of FIG. 8, taken along section line 9-9 of FIG. 8.

The surgical device 1 (FIG. 1) is used in an anastomosis procedure to effect joining of tissue (e.g., intestinal or other tubular organ sections). The anastomosis procedure is typically performed using minimally invasive surgical techniques including laparoscopic means and instrumentation. At the point in the anastomosis procedure shown in FIG. 8, in which the surgical device 1 (FIG. 1) is loaded with the loading 32 of FIG. 6, a diseased tissue section has been removed, the loading unit 32 and the anvil assembly 34 have been inserted (e.g., through surgical incisions or a body orifice) and positioned within respective first and second tissue sections T1, T2, the anvil shaft 36 (FIG. 1) has been connected to the elongated tubular body 24 (FIG. 1), and the anvil assembly 34 has been approximated towards the loading unit 32 to approximate the first and second tissue sections T1, T2. The surgical device 1 is actuated, as seen in FIG. 9, firing the staples 60 from the staple cartridge 42 and towards the anvil head 38 to effect stapling of the first and second tissue sections T1, T2 to one another, and the knife blade 59 cuts portions of the now stapled first and second tissue sections T1, T2 extending radially inwardly of the knife 58 to complete the anastomosis. Upon movement of the anvil assembly 34 away from the loading unit 32, the sensors 110, which are coupled via the tethers 70 to the staples 60 now secured to the first and second tissue sections T1, T2, are pulled out of the loading unit 32 and positioned adjacent to the stapled first and second tissue sections T1, T2, as seen in FIGS. 10 and 11.

Figure 10:
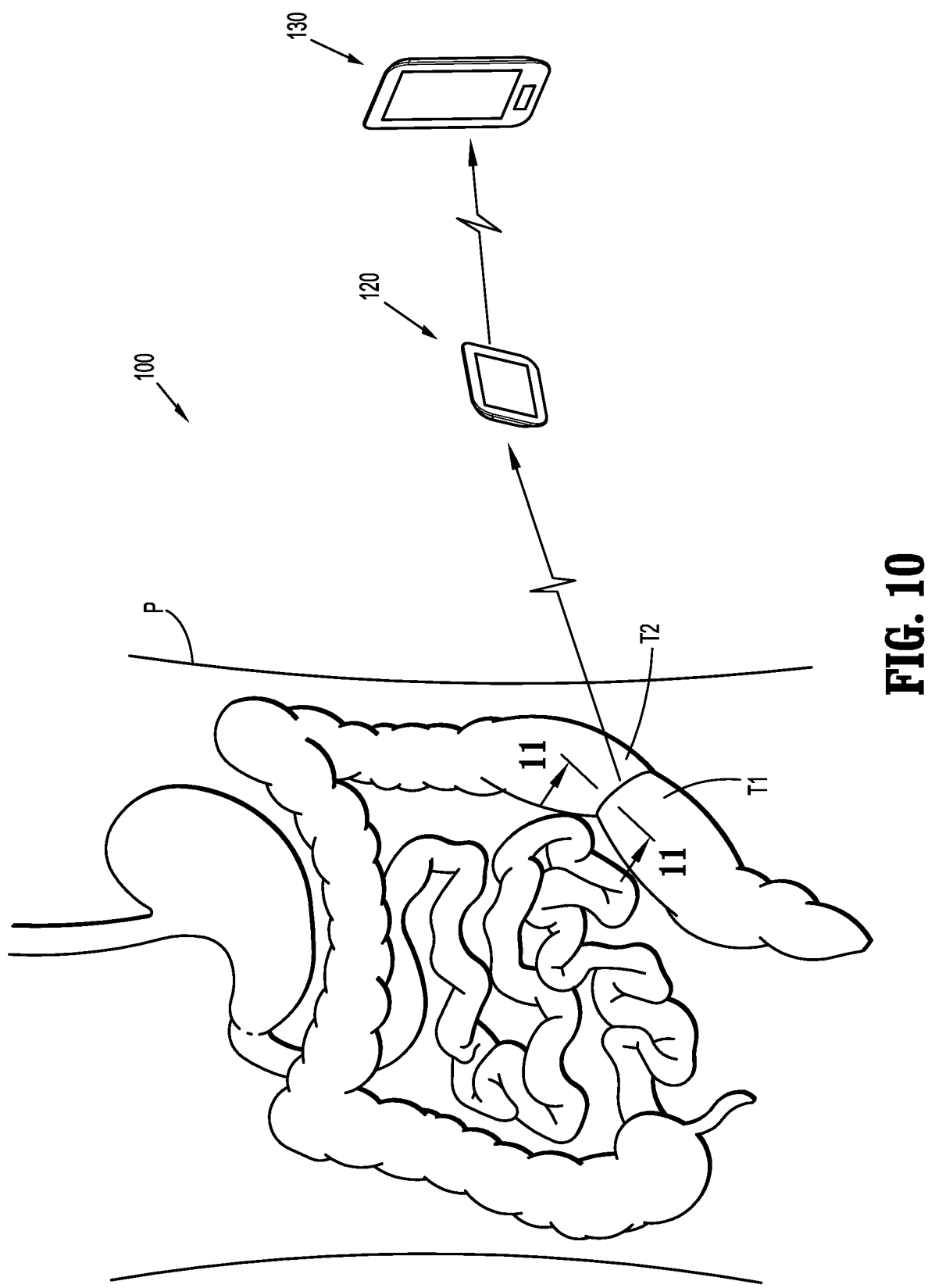
FIG. 10 is a system diagram of a tissue monitoring system in accordance with an aspect of the disclosure, including sensors implanted in the tissue by the end effector of FIG. 9.
Figure 11:
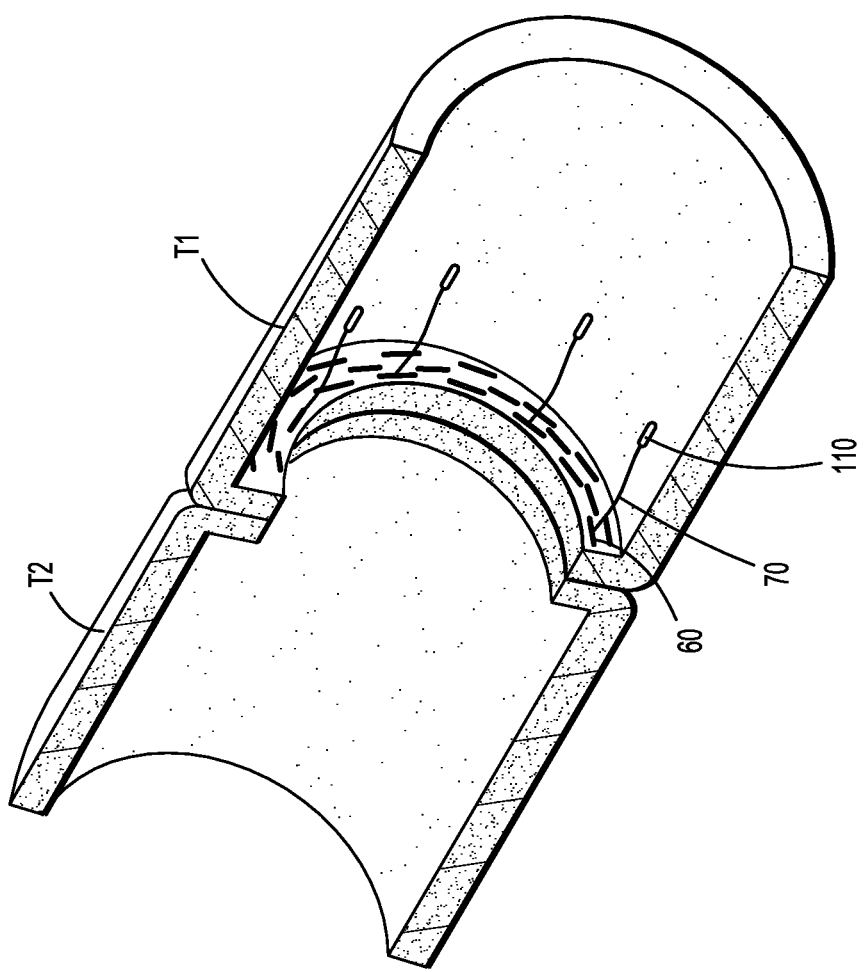
FIG. 11 is a cross-sectional view of the tissue of FIG. 10, taken along section line 11-11 of FIG. 10, shown after the tissue is stapled and the end effector is removed.

After the anastomosis is complete, and the surgical device 1 (FIG. 1) is removed from a patient P, as seen in FIGS. 10 and 11, a tissue monitoring system 100, including the sensors 110 now implanted in the patient P, is used to monitor the anastomosis. After monitoring is complete and the tethers 70 have degraded (e.g., after about a week), the sensors 110 are freed from the staples 60 and eliminated from the body of the patient P (e.g., in the patient's feces).

As shown in FIG. 10, in conjunction with FIG. 11, the monitoring system 100 is a local monitoring system that generally includes the sensors 110 (FIG. 11), a sensor reader 120, and a local computing device 130. As discussed above, the sensors 110 are implanted in a patient P adjacent to stapled tissue sections T1, T2 for measuring a physiological parameter of the tissue or tissue environment. The sensors 110 further convert the measurements into signals which are transmitted to the sensor reader 120 via a wireless communication link.

The sensor reader 120 is configured as an extracorporeal device for collecting data from the sensors 110. In some aspects, the sensor reader 120 is sized and shaped to be worn on the body of the patient P. The sensor reader 120 may be, for example, incorporated into a pendant, a wristwatch, a badge, etc., or may be housed within a carrying bag or pouch. In such aspects, the tissue monitoring system 100 allows for patient mobility and, in certain aspects, postsurgical monitoring at home. The sensor reader 120 transmits the signals from the sensors 110 to the local computing device 130 via a wireless communication link. In some other aspects, the sensor reader 120 is integrated into the local computing device 130.

The local computing device 130 is configured to receive and process the signals from the sensor reader 120 into physiological data and to display the physiological data. The local computing device 130 generally includes one or more processors and associated memories, hardware components (e.g., a communications hardware-module for communicating with the sensor reader), software (e.g., computer code stored in the memory and executed by the processor) for applications, such as, for example, receiving, processing and displaying the signals from the sensors as physiological data), and a display (e.g., a screen) to which the physiological data is outputted for viewing by the patient P and/or a clinician.

In some aspects, the local computing device 130 is a portable device, such as a laptop, a netbook, a tablet, a phone, and/or any other suitable device operable to send and receive signals, process the signals from the sensors 110 into physiological data, store and retrieve the signals and/or physiological data, and/or display the physiological data. In some other aspects, the local computing device 130 is a computer workstation (e.g., at a hospital). The local computing device 130 enables the patient P and/or a local clinician to monitor the collected physiological data.

The wireless communication link between the sensors 110, the sensor reader, 120, and the local computing device 130 may transmit data via, for example, frequencies appropriate for a personal area network (such as Bluetooth, WiFi, cellular, or infrared communications), or near-field, local, or wide area network frequencies, such as radio frequencies or medical body area network frequencies.

In a method of using the monitoring system 100, the sensors 110 are implanted in the patient P adjacent an anastomosis site, as described above. The sensor reader 120 is placed within sufficient proximity of the patient P to enable the sensor reader 120 to receive signals from the sensors 110. The patient P and/or a clinician monitors the physiological data on the local computing device 130. In some aspects, the local computing device 130 may provide an alert (e.g., a visual, audible, and/or haptic indication) when the physiological data is indicative of a complication.

The signals produced from the sensors 110 contain information about a specific characteristic of the tissue or tissue environment which, in turn, is processed into physiological data to impart information about the condition or state of the tissue or tissue environment. This information is used to determine a proper course of treatment dependent upon the physiological data received. For example, if one or more sensors 110 transmits information that meets a specified criterion indicating an abnormal physiological condition or state, a course of treatment may be selected, such as, for example, antibiotic therapy, surgical intervention, etc. On the other hand, if the information is within a range of a normal physiological condition or state, no further action is required on the part of the patient P or a clinician.

Figure 12:
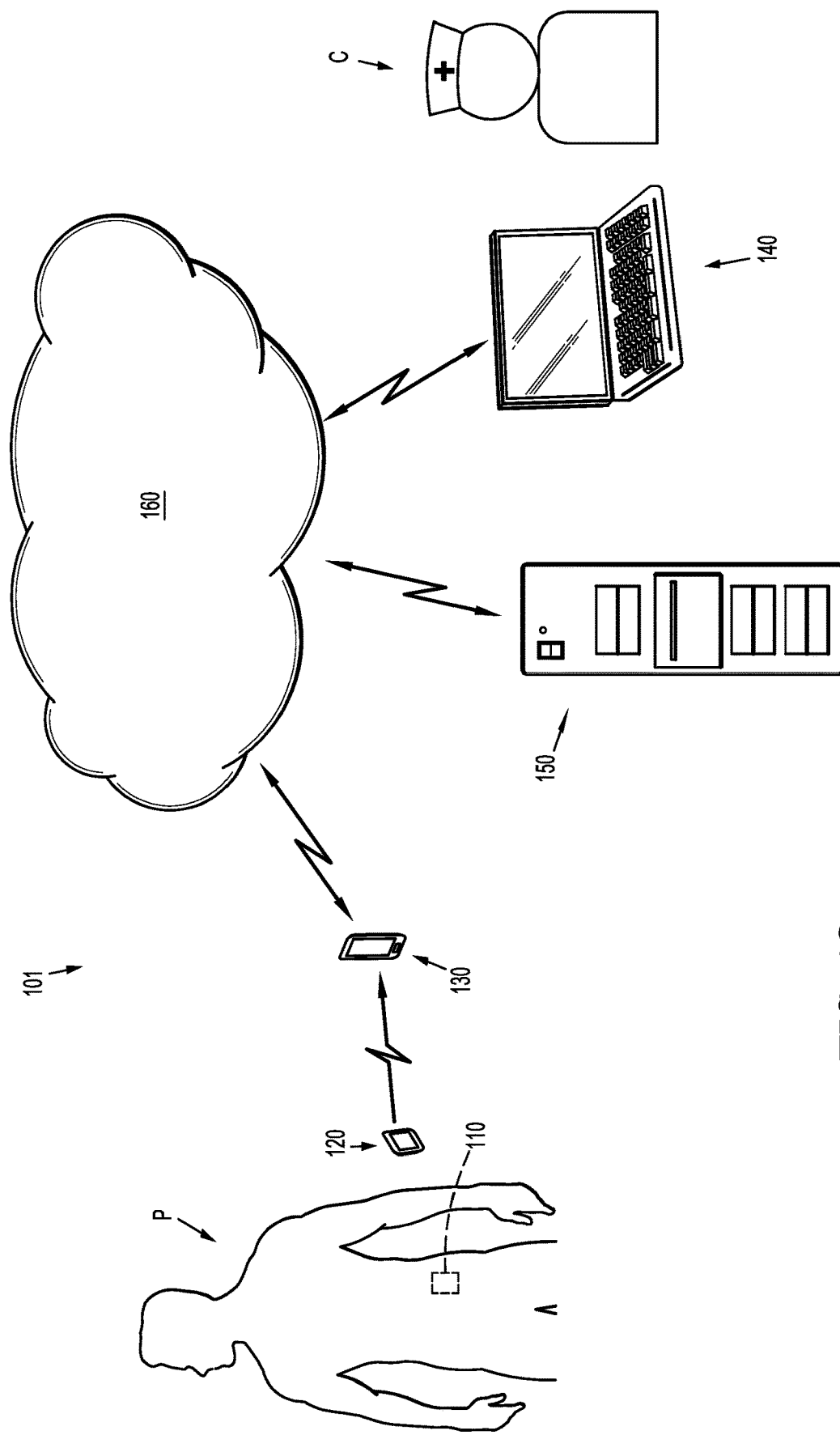
FIG. 12 is a system diagram of a tissue monitoring system in accordance with another aspect of the disclosure.

As shown in FIG. 12, a tissue monitoring system 101 in accordance with another aspect of the disclosure is shown. The tissue monitoring system includes the sensors 110, the sensor reader 120, and the local computing device 130, as described above with respect to the tissue monitoring system 100 of FIG. 10, and further includes a remote computing device 140, a server 150, and a network 160. The tissue monitoring system 101 allows for both local and remote monitoring of the anastomosis.

The local computing device 130, the remote computing device 140, and the server 150 are in communication with each other via the network 160, and each receives and/or sends signals over the network 160 via wireless communication links. The network 160 may be the internet, an intranet, a personal, local, or wide area network, etc. The remote computing device 140 may be functionally and/or structurally similar to the local computing device 130 such that the signals from the sensors 110 may be received, processed, and/or displayed by either or both the local and remote computing devices 130, 140, thereby enabling local and/or remote users (e.g., clinician C) to monitor the patient P. The server 150 may perform additional processing on the signals received from the sensors 110 and/or the physiological data received from the local or remote computing devices 130, 140, or may simply forward received information to the local and/or remote computers 130, 140. In some aspects, the server 150 may include databases storing information from sensors 110 implanted in a number of different patients, as well as, for example, electronic health records or personal health records of the patients.

The tissue monitoring system 101 enables real time monitoring of the physiological parameter of interest, such as temperature. For example, temperature readings are taken in real time and compared against self-historic temperature readings and trends to detect changes indicative of anastomotic leak. When a leak-like temperature pattern occurs, the tissue monitoring system 101 generates events to alert the clinician C and/or the patient P to take appropriate action (e.g., go to the hospital, contact the clinician, etc.). In some aspects, a rapid drop in temperature and/or a loss of signal indicates the sensors 110 have exited the body and the monitoring period has ended.

Figure 13:
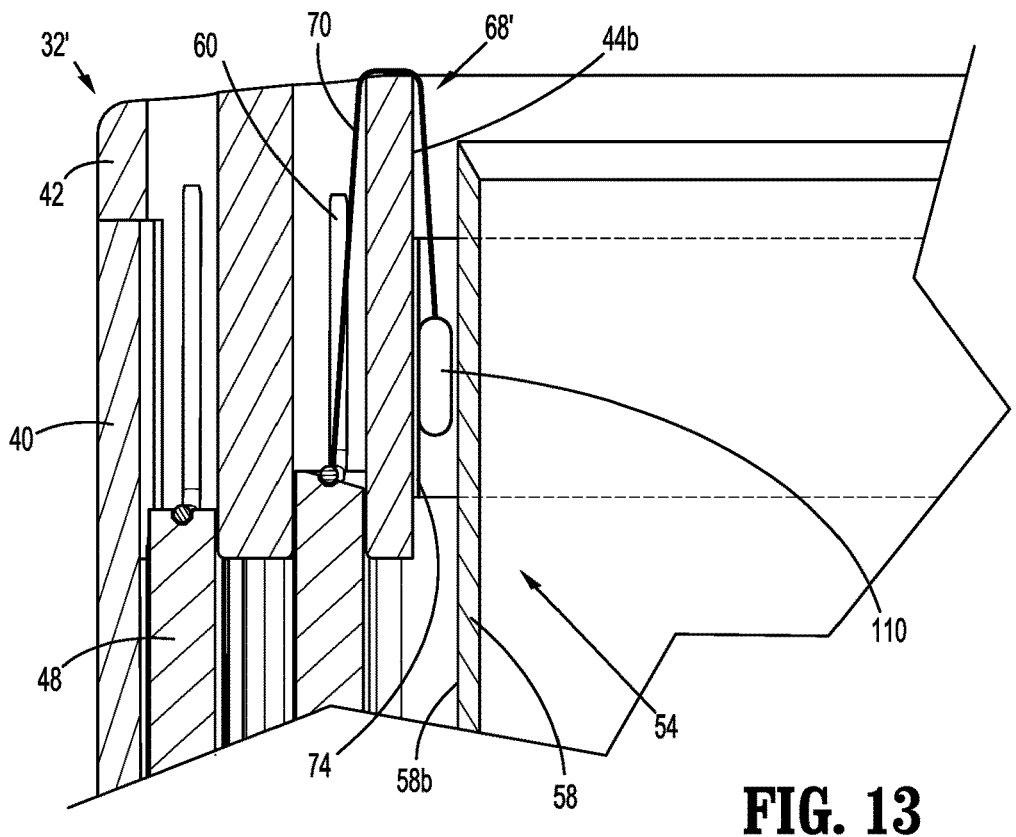
FIG. 13 is a partial cross-sectional view of a loading unit in accordance with another aspect of the disclosure.

Turning now to FIG. 13, a loading unit 32' in accordance with another aspect of the disclosure is shown. The loading unit 32' is substantially the same as the loading unit 32 of FIG. 1 and includes the housing 40, the staple cartridge 42, the staple pusher assembly 48, and the knife assembly 54. The loading unit 32', however, houses staples 60 including a sensor assembly 68'. The sensor assembly 68' includes one or more tethers 70, one or more sensors 110, and an annular band 74.

Figure 14:
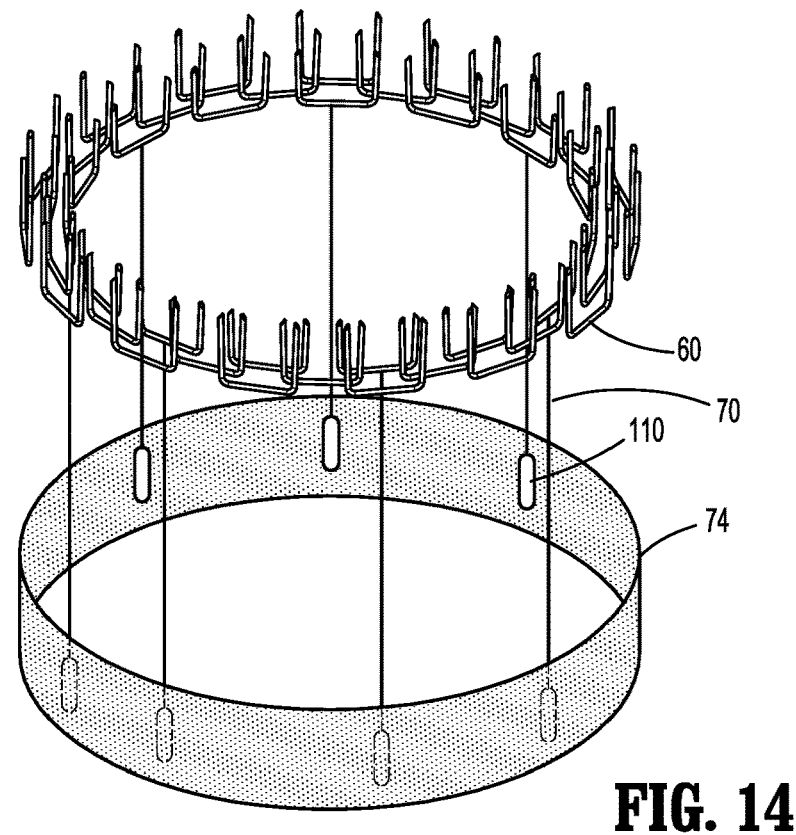
FIG. 14 is a perspective view of staples and a sensor assembly disposed within the loading unit of FIG. 13.

As shown in FIG. 14, the annular band 74 is a continuous loop of biocompatible material which is bioabsorbable or non-absorbable, natural or synthetic, or any combination thereof. In aspects, the annular band 74 is biodegradable, as described above with respect to the tether 70, such that the annular band 74 is broken down and excreted from the patient's body after a pre-determined period of time (e.g., short-term). In some aspects, the annular band 74 is formed from a self-expanding or spring-loaded material such that upon deployment from the loading unit 32' (FIG. 13), the annular band 74 deploys against and makes intimate contact with an inner wall of the tissue section within which it is placed. The annular band 74 may be a mesh, a film, and/or a buttress formed from porous and/or non-porous materials.

Figure 15:
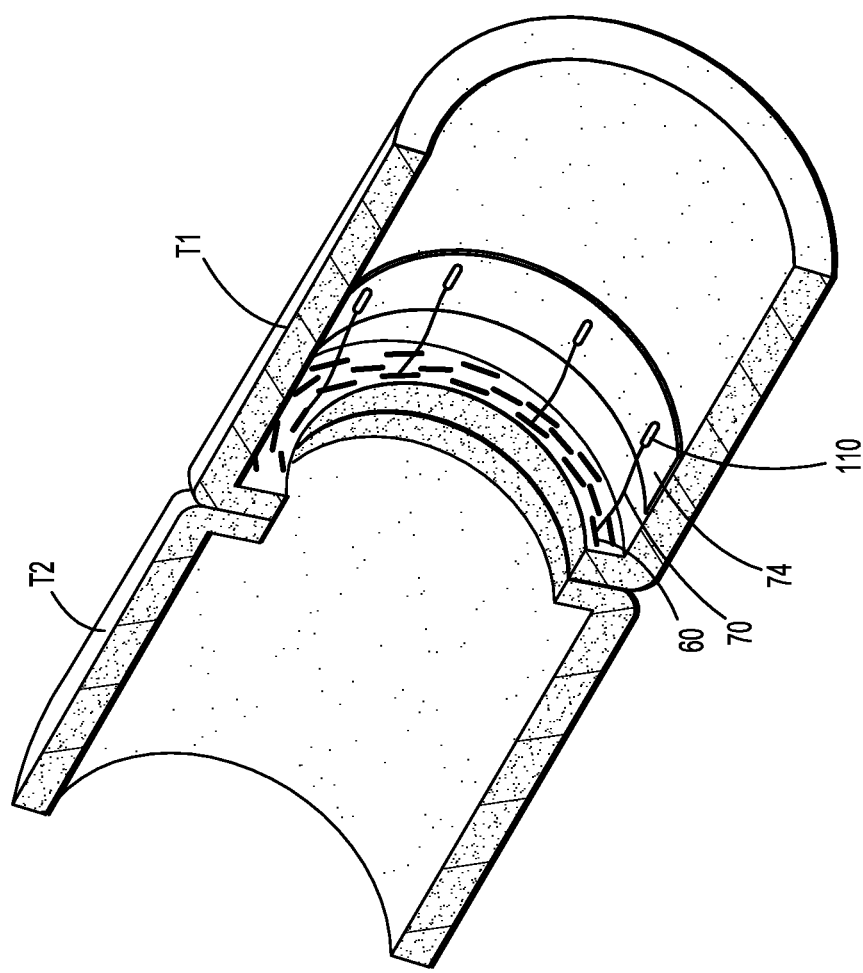
FIG. 15 is a cross-sectional view of tissue stapled using the loading unit of FIG. 13.

As seen in FIGS. 13 and 14, the annular band 74 is sized and shaped to fit between the inner side wall 44*b* of the staple cartridge 42 and the outer wall 58*b* of the knife 58 (e.g., against the inner side wall 44*b* of the staple cartridge 42), along with the sensors 110. The sensors 110 are releasably secured to the annular band 74 and disposed in radially spaced relation therearound. The sensors 110 may be secured to the annular band 74 by embedding the sensors 110 within the annular band 74, suturing the sensors 110 to the annular band 74, coupling the sensors 110 to the annular band 74 by a degradable adhesive or coating, among other techniques within the purview of those skilled in the art. Accordingly, after the anastomosis is performed, as shown in FIG. 15, the annular band 74 and the sensors 110 are disposed adjacent to the stapled tissue sections T1, T2 and against an inner wall of the tissue section T1.

Figure 16:
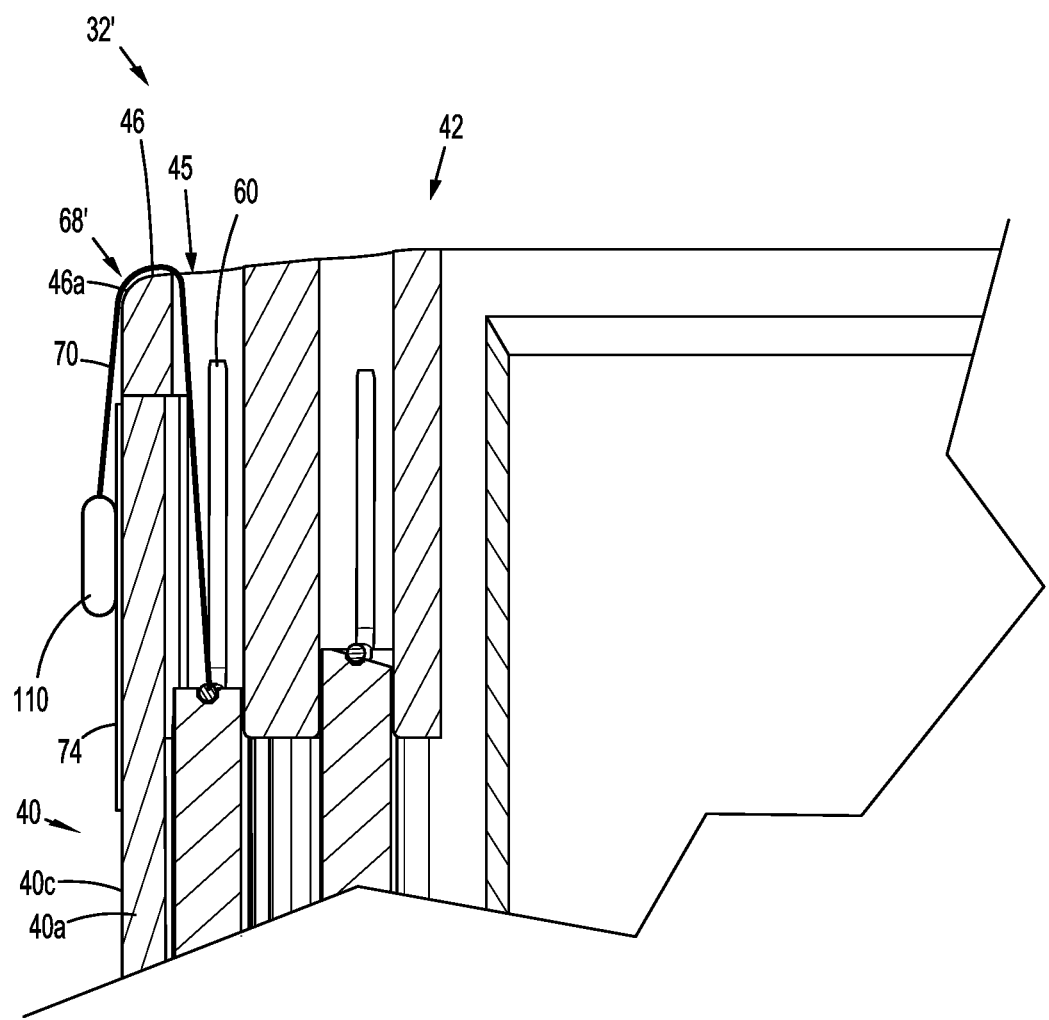
FIG. 16 is a partial cross-sectional view of a loading unit in accordance with yet another aspect of the disclosure.

Alternatively, as shown in FIG. 16, the annular band 74, with the sensors 110 releasably secured thereto, may be sized and shaped for positioning around the outer cylindrical portion 40*a* of the housing 40 of the loading unit 32'. In such aspects, the staples 60 including the sensor assembly 68' are disposed in the outermost row of staple pockets 45 and the tethers 70 extend out of the staple pockets 45, across the tissue facing surface 46, and over the outer edge 46*a* of the staple cartridge 42 such that the annular band 74 is disposed against an outer wall 40*c* of the housing 40.

Figure 17:
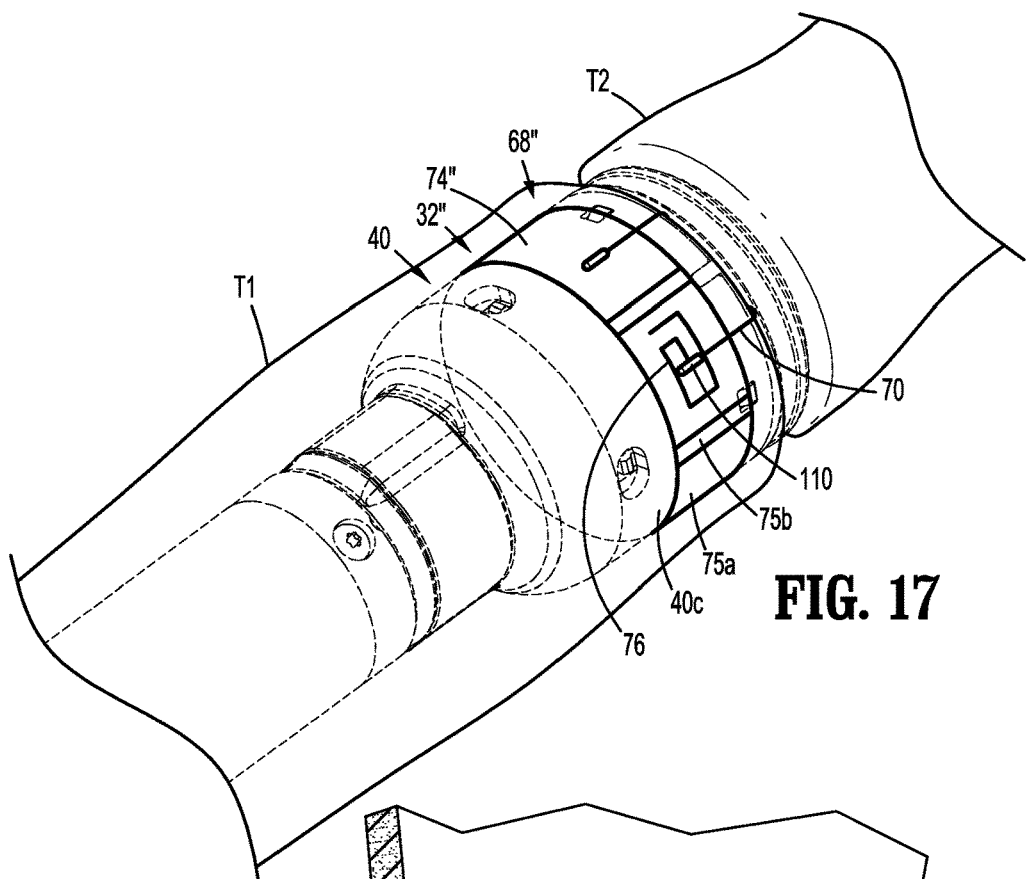
FIG. 17 is a perspective view of an end effector disposed within tissue, the end effector including a loading unit in accordance with another aspect of the disclosure.

Referring now to FIG. 17, a loading unit 32" in accordance with another aspect of the disclosure is shown. The loading unit 32" is substantially the same as the loading unit 32' of FIG. 16, except that the staple cartridge 42 (FIG. 18) housing the staples 60 (FIG. 18) includes a sensor assembly 68". The sensor assembly 68" includes one or more tethers 70, one or more sensors 110, and an annular band 74". The annular band 74" is sized and shaped for positioning around the outer wall 40*c* of the housing 40 of the loading unit 32". The annular band 74" has a discontinuous body 75*a* including breaks or gaps 75*b* defined therein to facilitate release from the loading unit 32". The annular band 74" further includes an antenna 76 (FIG. 19) attached to one or more of the sensors 110 for inductive power and communication of data from the sensors 110 to the sensor reader 120 (FIG. 10). The antenna 76 may be disposed (e.g., embedded) within the annular band 74", woven through the annular band 74", secured (e.g., via adhesives or coatings) to an inner or outer surface of the annular band 74", among other techniques within the purview of those skilled in the art.

Figure 18:
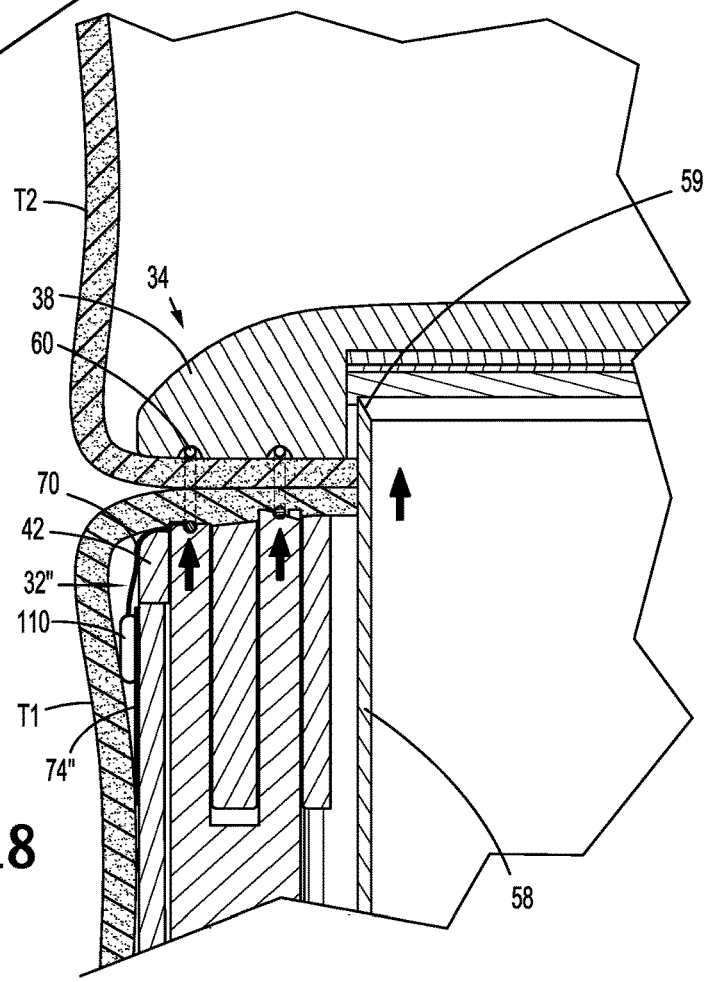
FIG. 18 is a partial cross-sectional view of the tissue and the end effector of FIG. 17.
Figure 19:
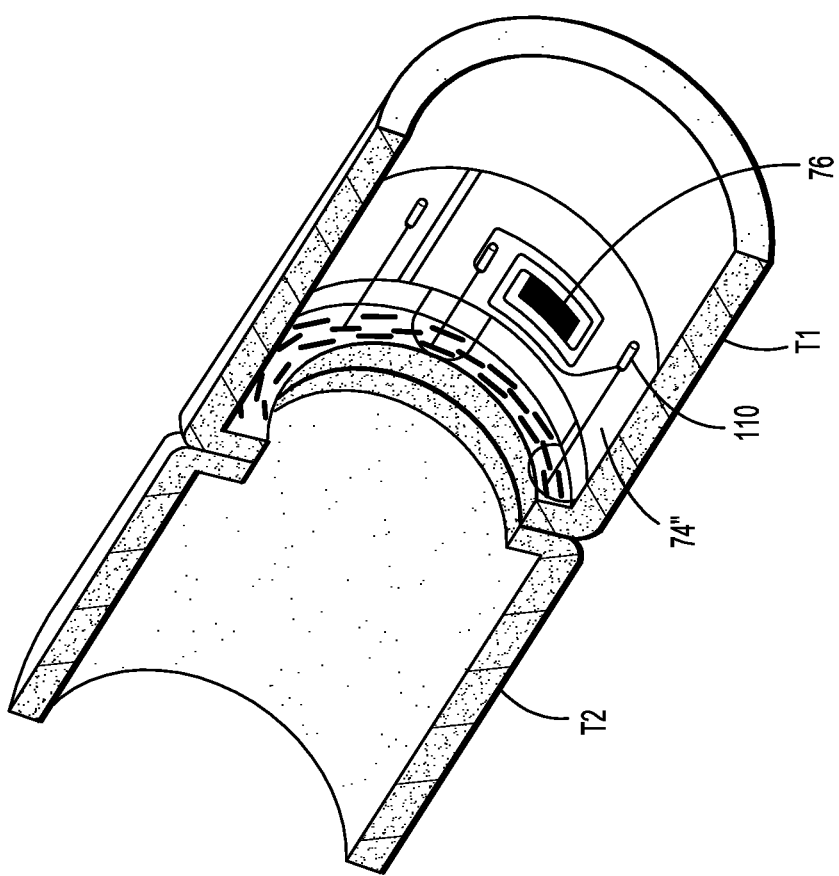
FIG. 19 is a cross-sectional view of the tissue of FIG. 18, shown after the tissue is stapled and the end effector is removed.

Once positioned within tissue sections T1, T2, the surgical device 1 (FIG. 1) is actuated, as shown in FIG. 18, firing the staples 60 from the staple cartridge 42 towards the anvil head 38 to effect stapling of the first and second tissue sections T1, T2 to one another, and the knife blade 59 cuts portions of the now stapled first and second tissue sections T1, T2 extending radially inwardly of the knife 58 to complete the anastomosis. Upon movement of the anvil assembly 34 away from the loading unit 32", the sensors 110, which are coupled to both the annular band 74" and the staples 60 (via the tethers 70), and are now secured to the first and second tissue sections T1, T2, are pulled out of the loading unit 32" and positioned adjacent to the stapled first and second tissue sections T1, T2. After the anastomosis is complete, as shown in FIG. 19, the annular band 74" and the sensors 110 are disposed adjacent to the stapled tissue sections T1, T2 and against an inner wall of the tissue section T1.

Figure 20:
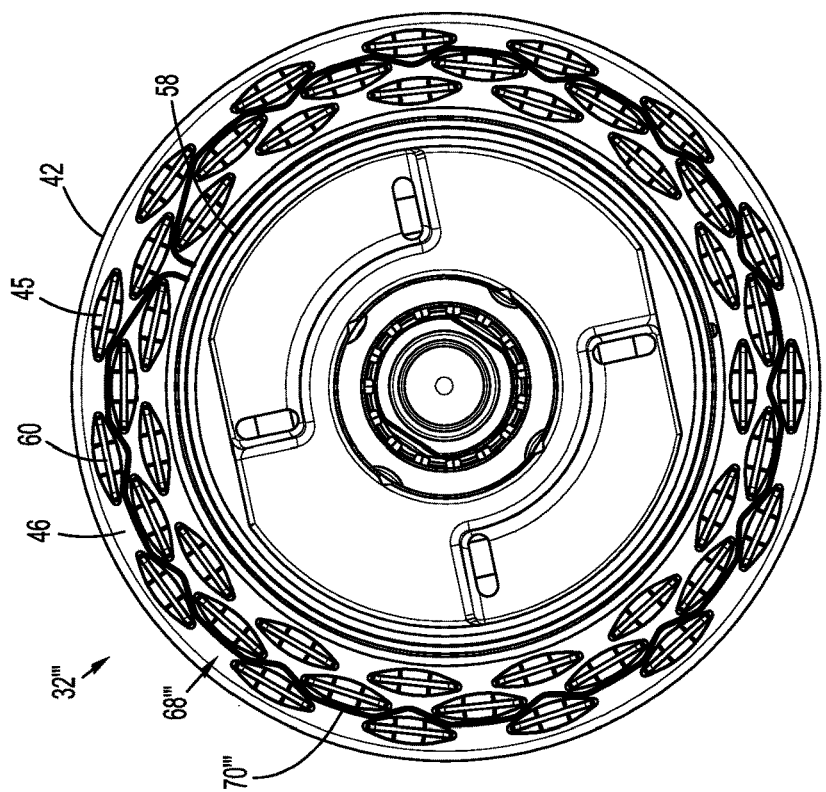
FIG. 20 is a top view of a loading unit in accordance with another aspect of the disclosure.

Referring now to FIG. 20, a loading unit 32''' in accordance with yet another aspect of the disclosure is shown. The loading unit 32''' is substantially the same as the loading unit 32 of FIG. 1, except that the loading unit 32''' includes a single sensor assembly 68''' that is not coupled to one of the staples 60. The sensor assembly 68''' includes a tether 70''' and a sensor 110''' (FIG. 21) coupled to the tether 70'''. The sensor 110''' is disposed between the staple cartridge 42 and the knife 58, as described above with regard to the sensors 110 of FIG. 6, however, the sensor 110''' may be disposed against the housing (not explicitly shown), as described above with regard to the sensors 110 of FIG. 7.

Figure 21:
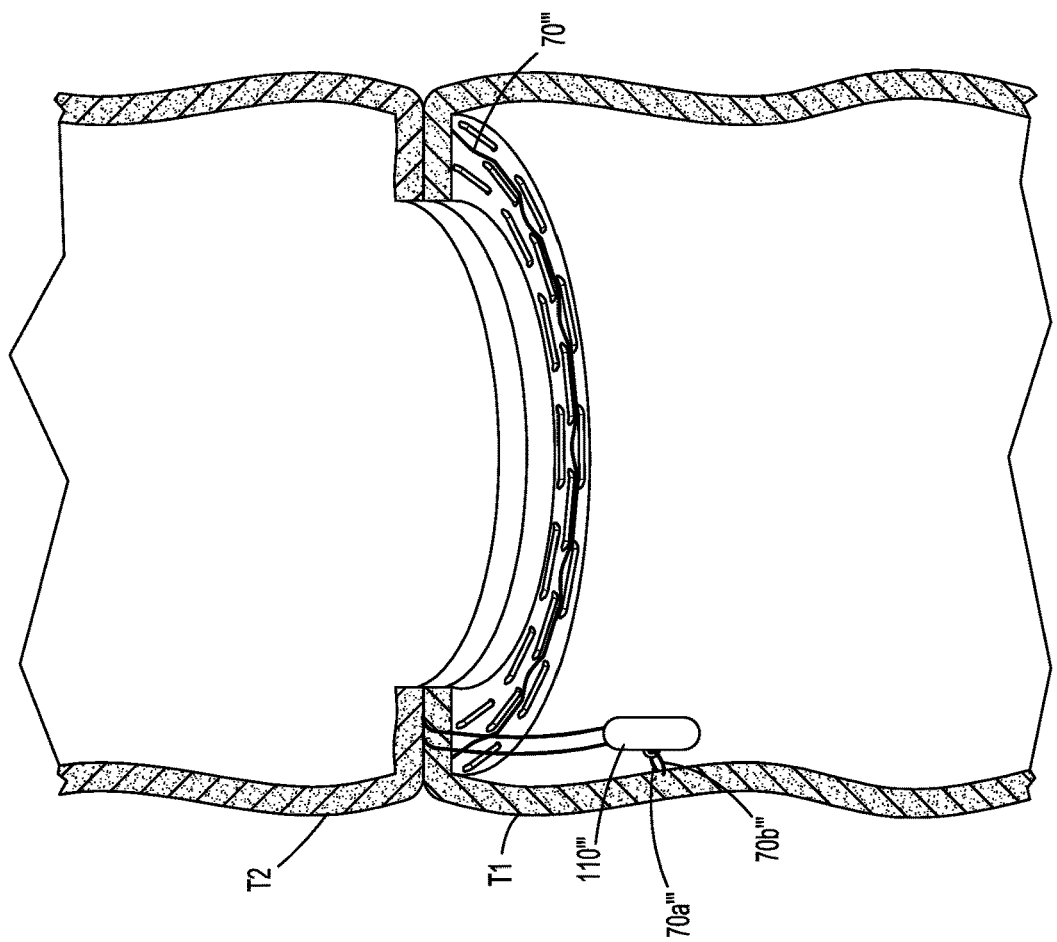
FIG. 21 is a cross-sectional view of tissue stapled using the loading unit of FIG. 20.

The tether 70''' is a conductive wire that is a releasably positioned on the tissue facing surface 46 of the staple cartridge 42 and the sensor 110''' is secured to the first and second end portions 70*a'''*, 70*b'''* (FIG. 21) of the tether 70'''. In aspects, the tether 70''' does not extend across any of the staple pockets 45 of the staple cartridge 42 and, in other aspects, the tether 70''' extends across at least one staple pocket 45 so that the tether 70''' is secured to tissue by at least one of the staples 60 during deployment from the loading unit 32'''. The impedance of the tether 70''' varies with temperature. Accordingly, after the anastomosis is performed, as shown in FIG. 21, and the tether 70''' is secured to the stapled first and second tissue sections T1, T2, pulses of known voltage values may be applied to the tether 70''' and the current is measured by the sensor 110''' (or pulse of known current are applied and the voltage is measured). The current (or voltage) will vary according to the temperature of the tissue sections T1, T2 such that the actual instantaneous temperature can be estimated.

It should be understood that one or more of the sensor assemblies 68, 68', 68", 68''' may be used together in a loading unit to measure physiological parameters, such as temperature, on the stapled tissue as well as adjacent to the stapled tissue by different monitoring modalities.

Additionally or alternatively, the anvil assembly 34 (FIG. 1) may include sensor assemblies. For example, the anvil assembly may include one or more sensor assemblies releasably secured thereto (e.g., to the anvil head) radially outwardly of the knife. In aspects in which sensor assemblies are also provided in the loading unit, once implanted, the sensors are able to take readings on opposed sides of the anastomosis.

While described as being used in colectomy procedures, it should be understood that the sensors of the disclosure may be utilized in any number of other surgeries that can benefit from early infection detection. The systems and methods may be used, for example, in low anterior resection, hemi-colectomy procedures, jejunostomy, roux-en-Y gastric bypass, hernia repair, and hysterectomy.

While illustrated as being used on a handheld powered surgical device hereinabove, it is contemplated, and within the scope of the disclosure for the end effector to be configured for use with handheld manually-actuated surgical devices, as well as other electrosurgical instruments. For example, the end effector may be configured to be detachably coupleable to (or permanently coupled in the case of disposable instruments) and controllable by a handheld manually actuated surgical device, such as those shown and described in U.S. Pat. Nos. 4,473,077 and 5,915,616, the entire content of each of which is incorporated herein by reference. As another example, the end effector may be configured to be detachably coupleable to and controllable by a robotic surgical system, such as the robotic surgical system shown and described in U.S. Patent Appl. Pub. No. 2012/0116416, the entire content of which is incorporated herein by reference.

While aspects of the disclosure have been shown in the drawings, it is not intended that the disclosure be limited thereto, as it is intended that the disclosure be as broad in scope as the art will allow and that the specification be read likewise. It is to be understood, therefore, that the disclosure is not limited to the precise aspects described, and that various other changes and modifications may be effected by one skilled in the art without departing from the scope or spirit of the disclosure. Additionally, the elements and features shown and described in connection with certain aspects of the disclosure may be combined with the elements and features of certain other aspects without departing from the scope of the disclosure, and that such modifications and variation are also included within the scope of the disclosure. Therefore, the above description should not be construed as limiting, but merely as exemplifications of aspects of the disclosure and the subject matter of the disclosure is not limited by what has been particularly shown and described. Thus, the scope of the disclosure should be determined by the appended claims and their legal equivalents, rather than by the examples given.

What is claimed is:

1. An end effector for a surgical device, the end effector including:
    a loading unit including a staple cartridge having staple pockets defined therein and staples disposed within the staple pockets, the loading unit including a sensor assembly coupled to one of the staples, the sensor assembly including a sensor and a tether interconnecting the sensor and the respective staple such that the sensor is spaced from the respective staple.

2. The end effector according to claim 1, wherein the staple cartridge has an annular configuration including an outer side wall and an inner side wall defining a central aperture therethrough.

3. The end effector according to claim 2, wherein the sensor of the sensory assembly is disposed within the central aperture of the staple cartridge.

4. The end effector according to claim 3, wherein the loading unit further includes a knife disposed within the central aperture of the staple cartridge, and the sensor is positioned between the inner side wall of the staple cartridge and an outer wall of the knife.

5. The end effector according to claim 4, wherein the staple cartridge includes a tissue facing surface extending across a distal end of the staple cartridge between the outer and inner side walls, and the tether of the sensor assembly extends out of the respective staple pocket, across a portion of the tissue facing surface, and into the central aperture.

6. The end effector according to claim 2, wherein the loading unit further includes a housing in which the staple cartridge is positioned, and the sensor of the sensory assembly is disposed against an outer wall of the housing.

7. The end effector according to claim 6, wherein the staple cartridge includes a tissue facing surface extending across a distal end of the staple cartridge between the outer and inner side walls, and the tether of the sensor assembly extends out of the respective staple pocket, across a portion of the tissue facing surface, and over an outer edge of the staple cartridge.

8. The end effector according to claim 2, wherein the sensor assembly further includes an annular band coupled to the sensor.

9. The end effector according to claim 8, wherein the annular band is positioned against the inner side wall of the staple cartridge.

10. The end effector according to claim 8, wherein the loading unit further includes a housing in which the staple cartridge is positioned, and the annular band is positioned around an outer wall of the housing.

11. The end effector according to claim 1, wherein the tether of the sensor assembly is formed from a bioabsorbable material.

12. The end effector according to claim 1, wherein the sensor is a temperature sensor.

13. A method of monitoring tissue, comprising:
    implanting a sensor into tissue, the sensor coupled to a staple by a tether and configured to measure a physiological parameter of the tissue, the sensor spaced from the staple by the tether; and
    monitoring the physiological parameter of the tissue on a computing device via information transmitted from the sensor to the computing device by a sensor reader.

14. The method according to claim 13, wherein implanting the sensor includes stapling the staple to the tissue.

15. A tissue monitoring system comprising:
    a sensor releasably coupled to a staple by a tether, the sensor configured to measure a physiological parameter of tissue and convert the measurement into a signal, the sensor spaced from the staple by the tether;
    a sensor reader configured to receive the signal from the sensor; and
    at least one computing device configured to receive the signal from the sensor reader and process the signal into physiological data.

16. The tissue monitoring system according to claim 15, wherein the at least one computing device includes a display for displaying the physiological data.

17. The tissue monitoring system according to claim 15, wherein the sensor reader is sized and shaped to be worn on a body of a patient.

18. The tissue monitoring system according to claim 15, wherein the sensor reader is integrated into the at least one computing device.

19. The tissue monitoring system according to claim 15, further comprising a server configured to store and process the physiological data.

20. The tissue monitoring system according to claim 19, further comprising a network through which signals are sent and received between the at least one computing device and the server.

* * * * *